US012673972B2

(12) United States Patent
Zahid

(10) Patent No.: US 12,673,972 B2
(45) Date of Patent: Jul. 7, 2026

(54) LUNG-SPECIFIC TARGETING-PEPTIDE (LTP), COMPOSITIONS, AND USES THEREOF

(71) Applicant: University of Pittsburgh—Of the Commonwealth System of Higher Education, Pittsburgh, PA (US)

(72) Inventor: Maliha Zahid, Gibsonia, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1076 days.

(21) Appl. No.: 17/731,965

(22) Filed: Apr. 28, 2022

(65) Prior Publication Data

US 2022/0315625 A1 Oct. 6, 2022

Related U.S. Application Data

(63) Continuation of application No. PCT/US2020/057850, filed on Oct. 29, 2020.

(60) Provisional application No. 62/984,925, filed on Mar. 4, 2020, provisional application No. 62/927,179, filed on Oct. 29, 2019.

(51) Int. Cl.
| | |
|---|---|
| *C07K 7/08* | (2006.01) |
| *A61K 9/00* | (2006.01) |
| *A61K 47/64* | (2017.01) |

(52) U.S. Cl.
CPC .............. *C07K 7/08* (2013.01); *A61K 9/0002* (2013.01); *A61K 47/64* (2017.08)

(58) Field of Classification Search
CPC .................................. C07K 7/64; A61K 38/12
See application file for complete search history.

(56) References Cited

U.S. PATENT DOCUMENTS

| | | | |
|---|---|---|---|
| 5,911,983 | A | 6/1999 | Barranger et al. |
| 8,258,257 | B2 | 9/2012 | Lo et al. |
| 9,249,184 | B2 * | 2/2016 | Robbins ................... C07K 7/06 |
| 9,387,257 | B2 | 7/2016 | Wu et al. |
| 2002/0061299 | A1 | 5/2002 | French |
| 2010/0221235 | A1 | 9/2010 | Arranz |
| 2010/0310495 | A1 | 12/2010 | Schneider et al. |
| 2012/0244136 | A1 | 9/2012 | Robbins et al. |
| 2015/0065434 | A1 | 3/2015 | Woster et al. |
| 2015/0328315 | A1 | 11/2015 | Kalifa et al. |
| 2016/0083431 | A1 * | 3/2016 | Fischer ................... A61P 11/00 |
| | | | 514/21.1 |
| 2016/0106800 | A1 | 4/2016 | Szeto et al. |
| 2018/0141977 | A1 | 5/2018 | Otterlei et al. |
| 2018/0354993 | A1 | 12/2018 | Urban et al. |
| 2019/0211061 | A1 | 7/2019 | Fischer et al. |
| 2019/0300571 | A1 | 10/2019 | Cudic et al. |
| 2021/0085790 | A1 * | 3/2021 | Hopkins ............ A61K 41/0071 |
| 2021/0206805 | A1 | 7/2021 | Zahid |

FOREIGN PATENT DOCUMENTS

| | | | |
|---|---|---|---|
| CN | 102766258 | A | 11/2012 |
| WO | WO-2003/079972 | A2 | 10/2003 |
| WO | WO-2008/045976 | A2 | 4/2008 |
| WO | WO-2010/033868 | A2 | 3/2010 |
| WO | WO-2019/038562 | A1 | 2/2019 |
| WO | WO-2019226785 | A1 * | 11/2019 .............. C07K 7/06 |
| WO | WO-2020210712 | A2 * | 10/2020 ......... A61K 47/6929 |

OTHER PUBLICATIONS

Arap et al., "Cancer Treatment by Targeted Drug Delivery to Tumor Vasculature in a Mouse Model", *Science*, 279(5349):377-380, Jan. 1998.
Choi et al. (2020), "Recent Trends in Cyclic Peptides as Therapeutic Agents and Biochemical Tools," *Biomol Ther.* 28(1):18-24.
Frantz et al., "Absence of NF-κB Subunit p50 Improves Heart Failure after Myocardial Infarction", *The FASEB Journal*, 20(11):1918-1920, Sep. 2006.
He et al. (2019), "Peptide Conjugates with Small Molecules Designed to Enhance Efficacy and Safety," *Molecules* 24(1855).
International Search Report and Written Opinion for PCT/US2020/057850 mailed Feb. 9, 2021, 12 pages.
Jiang et al., "Acute Protection of Ischemic Heart by FGF-2: Involvement of FGF-2 Receptors and Protein Kinase C", *Am J Physiol Heart Circ Physiol*, 282(3):H1071-H1080, Mar. 2002.
Kamide et al. (2010) "Isolation of novel cell-penetrating peptides from a random peptide library using in vitro virus and their modifications," International Journal of Molecular Medicine 25:41-51.
Kawano et al., "Blockade of NF-κB Improves Cardiac Function and Survival after Myocardial Infarction", *Am. J Physiol Heart Circ Physiol*, 291:H1337-H1344, 2006.
Kelly et al., "In Vivo Phage Display Selection Yields Atherosclerotic Plaque Targeted Peptides for Imaging", Molecular Imaging and Biology, 8(4):201-207, 2006.
Li et al., "Gene Therapy with Extracellular Superoxide Dismutase Protects Conscious Rabbits Against Myocardial Infarction", *Circulation*, 103(14):1893-1898, Apr. 2001.
Li et al., "Gene Therapy with iNOS Provides Long-Term Protection Against Myocardial Infarction Without Adverse Functional Consequences", *Am J Physiol Heart Circ Physiol*, 290(2):H584-H589, Feb. 2006.

(Continued)

*Primary Examiner* — Christina Bradley
(74) *Attorney, Agent, or Firm* — The Webb Law Firm

(57) ABSTRACT

Disclosed is a synthetic, non-naturally occurring 12-amino acid peptide, Lung-specific Targeting Peptide, belonging to the larger class of cell penetrating peptides, for delivery of both diagnostic and potentially therapeutic agents to the lung. Also disclosed are methods of treating pulmonary disease, e.g., chronic obstructive pulmonary disease (COPD), emphysema, chronic bronchitis, asthma, primary ciliary dyskinesia (PCD), cystic fibrosis (CF), and lung cancer.

14 Claims, 13 Drawing Sheets

Specification includes a Sequence Listing.

(56) References Cited

OTHER PUBLICATIONS

Lu et al., "Targeting of Embryonic Stem Cells by Peptide-Conjugated Quantum Dots", *PloS ONE*, 5(8):e12075, Aug. 2010.

McGuire et al., "In vitro Selection of a Peptide with High Selectivity for Cardiomyocytes In vivo", *Journal of Molecular Biology*, 342(1):171-182, Sep. 2004.

Melo et al., "Gene Therapy Strategy for Long-Term Myocardial Protection Using Adeno-Associated Virus-Mediated Delivery of Heme Oxygenase Gene", *Circulation*, 105(5):602-607, Feb. 2002.

Mi et al., "Identification of a Synovial Fibroblast-Specific Protein Transduction Domain for Delivery of Apoptotic Agents to Hyperplastic Synovium", *Molecular Therapy*, 8(2):295-305, Aug. 2003.

Molenaar et al., "Uptake and Processing of Modified Bacteriophage M13 in Mice: Implications for Phage Display", *Virology*, 293(1):182-191, Feb. 2002.

Okada et al, "Postinfarction Gene Therapy Against Transforming Growth Factor-ß signal Modulates Infarct Tissue Dynamics and Attenuates Left Ventricular Remodeling and Heart Failure", *Circulation*, 111(19):2430-2437, May 2005.

Pachori et al. (2004) "Hypoxia-regulated Therapeutic Gene as a Preemptive Treatment Strategy Against Ischemia/Reperfusion Injury," PNAS 101(33):12282-12287.

Pasqualini et al., "Organ Targeting In Vivo Using Phage Display Peptide Libraries", *Nature*, 380(6572):364-366, Mar. 1996.

Pleger et al., "S100A1 Gene Therapy Preserves in Vivo Cardiac Function after Myocardial Infarction", *Molecular Therapy*, 12(6):1120-1129, Dec. 2005.

Rogers et al., "Temporal Trends in the Treatment of Over 1.5 Million Patients With Myocardial Infarction in the U.S. from 1990 Through 1999: The National Registry of Myocardial Infarction 1, 2 and 3", *Journal of the American College of Cardiology*, 36(7):2056-2063, Dec. 2000.

Roncalli et al., "Sonic Hedgehog-Induced Functional Recovery After Myocardial Infarction Is Enhanced by AMD3100-Mediated Progenitor-Cell Mobilization", *Journal of the American College of Cardiology*, 57(24):2444-2452, Jun. 2011.

Rákos et al., "Evans Blue Fluorescence Permits the Rapid Visualization of Non-Intact Cells in the Perilesional Rim of Cold-Injured Rat Brain", *Acta Neurobiologiae Experimentals (Wars.)*, 67(2):149-154, 2007.

Segvich et al., "Identification of Peptides with Targeted Adhesion to Bone-Like Mineral via Phage Display and Computational Modeling", *Cells Tissue Organs*, 189(1-4):245-251, 2009.

Segvich et al., "The Absorption of Preferential Binding Peptides to Apatite-Based Materials", *Biomaterials*, 30(7):1287-1298, Mar. 2009.

Szeto HH, (2006) "Cell-permeable, Mitochondrial-targeted, Peptide Antioxidants," The AAPS Journal 8(2):E277-E283.

Traboulsi et al. (2015) "Macrocyclic Cell Penetrating Peptides: A Study of Structure-Penetration Properties," Bioconjugate Chemistry 26(3):405-411.

Vrettos et al. (2018), "On the design principles of peptide-drug conjugates for targeted drug delivery to the malignant tumor site," *J Org Chem*. 14:930-954.

Wiviott et al., "Performance of the Thrombolysis In Myocardial Infarction Risk Index in the National Registry of Myocardial Infarction-3 and -4: A Simple Index That Predicts Mortality in ST-Segment Elevation Myocardial Infarction", *Journal of the American College of Cardiology*, 44(4):783-789, Aug. 2004.

Yao et al., "Targeting Pancreatic Islets with Phage Display Assisted by Laser Pressure Catapult Microdissection", *American Journal of Pathology*, 166(2):625-636, Feb. 2005.

Zahid et al., Aug. 17, 2010, Identification of a Cardiac Specific Protein Transduction Domain by In Vivo Biopanning using a M13 Phage peptide Display Library in Mice, PLoS ONE, 5(8): 11 pages.

Zahid, 2009, Targeting the Heart Using In Vivo Phage Display, University of Pittsburgh, Doctoral thesis, 132 pages.

Zahid, et al. (2016) "Targeting the Heart Utilizing a Novel Cell Penetrating Peptide," International Academy of Cardiology, Annual Scientific Sessions 2016 21st World Congress on Heart Disease. Conference Abstract (Online) p. 42.

Zahid, et al. (2017) "A Novel Cell Penetrating Peptide, Cardiac Targeting Peptide Appears to Utilize Cardiac Channels for Transduction." International Academy of Cardiology, Annual Scientific Sessions 2017 22nd World Congress on Heart Disease. Conference abstract (online) p. 40.

Zhang et al., "Molecular Profiling of Heart Endothelial Cells", *Circulation*, 112(11):601-611, Sep. 2005.

Mousavizadeh et al. "Cell targeting peptides as smart ligands for targeting of therapeutic or disgnostic agents: a systematic review," 158:507-517, 2017.

\* cited by examiner 0 min 10uM                    30 min 5uM                    30 min 10uM 0 min 10uM                    30 min 5uM                    30 min 10uM 0 min 10uM                    30 min 5uM                    30 min 10uM 0 min 10uM                    30 min 5uM                    30 min 10uM

LUNG-SPECIFIC TARGETING-PEPTIDE (LTP), COMPOSITIONS, AND USES THEREOF

CROSS-REFERENCE TO RELATED APPLICATIONS

This application is a continuation of International Application No. PCT/US2020/057850, with an international filing date of Oct. 29, 2020, which claims the benefit of and priority to U.S. Provisional Patent Application No. 62/927,179, filed on Oct. 29, 2019 and U.S. Provisional Patent Application No. 62/984,925, filed on Mar. 4, 2020, the disclosure of each of which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Apr. 27, 2022, is named UPB-019WOC1_SL_ST25.txt and is 6,396 bytes in size.

FIELD OF THE INVENTION

The invention relates generally to lung-specific targeting peptide ("LTP")-mediated delivery of molecular cargoes specifically to cells of the lung.

BACKGROUND

Although developments have been made to date, there is still an ongoing need for new and effective methodologies to target lung tissue specifically for delivery of biologics and/or cargo of therapeutic potential.

SUMMARY OF THE INVENTION

In one aspect, the present disclosure provides a method of introducing a drug or therapeutic, a nanoparticle, a peptide, a protein, a nucleic acid, or a detectable agent into a lung epithelial cell, comprising administering to the lung epithelial cell a twelve amino acid Lung-specific Targeting-Peptide ("LTP") having a sequence of Ala-Pro-Trp-His-Leu-Ser-Ala-Gln-Tyr-Ser-Arg-Thr (S7A, SEQ ID NO: 1) or Ala-Pro-Trp-His-Leu-Ser-Ser-Gln-Tyr-Ser-Ala-Thr (R11A, SEQ ID NO: 2) connected to the drug or therapeutic, nanoparticle, peptide, protein, nucleic acid, or detectable agent.

In one aspect, the present disclosure provides a compound comprising a recombinant and isolated Lung-specific Targeting-Peptide ("LTP") of the sequence of SEQ ID NO: 1 or 2. In some embodiments, the LTP is optionally further connected to a label at the N- and/or the C-termini. In some embodiments, the LTP is optionally further connected to a label at the C-terminus. In some embodiments, the compound is formulated as a delivery vehicle/agent. In some embodiments, the LTP is conjugated to a drug or therapeutic, a nanoparticle, a peptide, a protein, a nucleic acid, or a detectable agent. In some embodiments, the LTP is conjugated to the drug or therapeutic, the nanoparticle, the peptide, the protein, the nucleic acid, or the detectable agent via an ester linkage, disulfide or protease sensitive linkers. In some embodiments, the LTP is linked to a nucleic acid for gene therapy.

In some embodiments, the LTP is conjugated to a nanoparticle, which comprises a drug or therapeutic. In some embodiments, the LTP is linked to an ROS scavenger molecule. In some embodiments, the LTP is linked to a ROS scavenger molecule selected from the group consisting of glutathione (GSH), Szeto-Schiller peptide (SS-31), Mito-tempo, catalase, and superoxide dismutase. In some embodiments, the ROS scavenger is linked upstream of the N-terminus of the LTP peptide. In some embodiments, an ester linkage links the LTP and the ROS scavenger. In some embodiments, the ester linkage is an ester linkage cleavable by an intracellular esterase.

In some embodiments, the LTP is linked to a γ-secretase inhibitor or a Notch inhibitor.

In some embodiments, the LTP is linked to N—[N-(3,5-difluorophenacetyl-L-alanyl)]-S-phenylglycine t-butyl ester (DAPT).

In some embodiments, the LTP is a linear peptide. In some embodiments, the LTP is a cyclic peptide.

In another aspect, the present disclosure provides a formulation comprising a Lung-specific Targeting Peptide (LTP) of the sequence of SEQ ID NO: 1 or 2 connected to a drug or therapeutic, nanoparticle, peptide, protein, nucleic acid, or detectable agent, and a pharmaceutically acceptable carrier. In some embodiments, the LTP is optionally further connected to a label at the N- and/or the C-termini. In some embodiments, the LTP is optionally further connected to a label at the C-terminus.

In some embodiments, the LTP is conjugated to the drug or therapeutic, a nanoparticle, a peptide, a protein, a nucleic acid, or a detectable agent. In some embodiments, the LTP is conjugated to the drug or therapeutic, the nanoparticle, the peptide, the protein, the nucleic acid, or the detectable agent via an ester linkage, disulfide or protease sensitive linkers.

In some embodiments, the nanoparticle comprises a drug or therapeutic. In some embodiments, the LTP is connected to a nucleic acid for gene therapy, a small interfering RNA (siRNA), a small nuclear RNA (snRNA), a non-coding RNA), a microRNA (miRNA), a messenger RNA (mRNA), a catalytic RNA, a catalytic DNA, a DNA origami, an antisense oligonucleotide (ASO), a nucleoside analogs, a polynucleic acid decoy, an aptamer, a plasmid, or a nucleic acid vector. In some embodiments, the LTP is connected to a ROS scavenger molecule or a γ-secretase inhibitor or a Notch inhibitor. In some embodiments, the ROS scavenger molecule is selected from the group consisting of gluta-thione (GSH), Szeto-Schiller peptide (SS-31), Mitotempo, catalase and superoxide dismutase; and wherein the γ-secretase inhibitor or the Notch inhibitor is N—[N-(3,5-difluorophenacetyl-L-alanyl)]-S-phenylglycine t-butyl ester (DAPT). In some embodiments, the ROS scavenger, or the γ-secretase inhibitor or the Notch inhibitor is connected upstream of the N-terminus of the LTP peptide. In some embodiments, the connection comprises an ester linkage between the LTP and the ROS scavenger, or the γ-secretase inhibitor or the Notch inhibitor. In some embodiments, the ester linkage is an ester linkage cleavable by an intracellular esterase. In some embodiments, the LTP is a linear peptide. In some embodiments, the LTP is a cyclic peptide.

In some embodiments, the formulation is a sustained-delivery formulation. In some embodiments, the formulation uses a controlled release system. In some embodiments, the formulation uses a slow release system.

In another aspect, the present disclosure provides a method of treating a human subject suffering from lung disease or disorder, the method of the above embodiments or the formulation of the above embodiments. In some embodiments, the subject suffers from a lung disease or disorder selected from the group consisting of chronic obstructive pulmonary disease (COPD), emphysema, chronic bronchitis, asthma, primary ciliary dyskinesia (PCD), cystic fibrosis (CF), and lung cancer. In some embodiments, the subject suffers from chronic obstructive pulmonary disease (COPD). In some embodiments, the subject suffers from asthma. In some embodiments, the subject suffers from cystic fibrosis (CF). In some embodiments, the subject suffers from lung cancer.

In another aspect, the present disclosure provides a method of growing and/or re-cilliating tracheal epithelial cells (MTCs) and/or nasal epithelial cells of a mammal, the method comprising the method of the above embodiments, or the formulation of the above embodiments.

In another aspect, provided herein is a cyclic peptide comprising an amino acid sequence of any one of SEQ ID NOs: 1-14, wherein an N-terminal lysine is added to the amino acid sequence, wherein the N-terminal lysine connects to the C-terminus of the amino acid sequence.

In some embodiments, the N-terminal lysine chemically bonds to the C-terminus of the amino acid sequence. In some embodiments, the chemical bond is between the alpha-amino group of the N-terminal Lysine and the C-terminus of the amino acid sequence. In some embodiments, the cyclic peptide is optionally further connected to a label at the N- and/or the C-termini. In some embodiments, the cyclic peptide is optionally further connected to a label at the N-terminus.

In some embodiments, the cyclic peptide is formulated as a delivery vehicle/agent. In some embodiments, the cyclic peptide is conjugated to a drug or therapeutic, a nanoparticle, a peptide, a protein, a nucleic acid, or a detectable agent. In some embodiments, the cyclic peptide is conjugated to the drug or therapeutic, the nanoparticle, the peptide, the protein, the nucleic acid, or the detectable agent via an ester linkage, disulfide or protease sensitive linkers. In some embodiments, the nanoparticle comprises a drug or therapeutic. In some embodiments, the cyclic peptide is connected to a nucleic acid for gene therapy, a small interfering RNA (siRNA), a small nuclear RNA (snRNA), a non-coding RNA), a microRNA (miRNA), a messenger RNA (mRNA), a catalytic RNA, a catalytic DNA, a DNA origami, an antisense oligonucleotide (ASO), a nucleoside analogs, a polynucleic acid decoy, an aptamer, a plasmid, or a nucleic acid vector. In some embodiments, the cyclic peptide is connected to a ROS scavenger molecule or a γ-secretase inhibitor or a Notch inhibitor. In some embodiments, the ROS scavenger molecule is selected from the group consisting of glutathione (GSH), Szeto-Schiller peptide (SS-31), Mitotempo, catalase and superoxide dismutase; and wherein the γ-secretase inhibitor or the Notch inhibitor is N—[N-(3,5-difluorophenacetyl-L-alanyl)]-S-phenylglycine t-butyl ester (DAPT). In some embodiments, the ROS scavenger, or the γ-secretase inhibitor or the Notch inhibitor is connected upstream of the N-terminus of the cyclic peptide. In some embodiments, the cyclic peptide comprises an ester linkage between the cyclic peptide and the ROS scavenger, or the γ-secretase inhibitor or the Notch inhibitor. In some embodiments, the ester linkage is an ester linkage cleavable by an intracellular esterase.

In another aspect, provided herein is a formulation comprising the cyclic peptide described herein.

Various aspects and embodiments of the invention are described in further detail below.

BRIEF DESCRIPTION OF THE DRAWINGS

The invention can be more completely understood with reference to the following drawings.

FIG. 5A shows fluorescence intensity lung-to-liver ratio and standard deviation; FIG. 5B shows fluorescence intensity lung-to-liver ratio and standard error of the mean.

DETAILED DESCRIPTION

Figure 1:
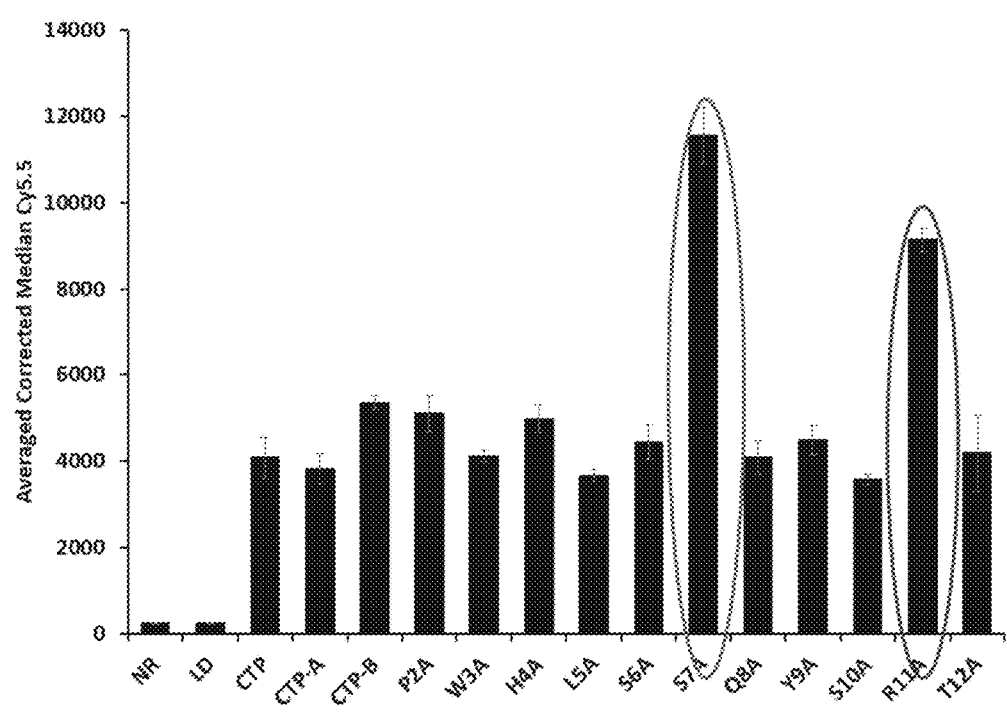
FIG. 1 shows bar graphs depicting median fluorescent intensities from fluorescence activated cell sorting (FACS) of H9C2 cardiomyoblast cells incubated with fluorescently-labeled peptides.

The invention is based, in part, upon the discovery of two lung-specific targeting-peptides (LTP) with efficient lung-tissue specific transduction/cell penetration property, and, in effect, efficient lung-tissue specific cargo-delivery and therapeutic properties. The present disclosure provides that the LTP of the present disclosure would be advantageous in delivering a cargo and/or a therapeutic agent to the lung tissue of a mammalian subject (e.g., human).

Various features and aspects of the invention are discussed in more detail below.

I. Lung-Specific Targeting Peptide (LTP)

The LTP of any one of SEQ ID NOs: 1-2 is a recombinant or synthetically prepared peptide.

The present disclosure provides for Lung-specific Targeting Peptides ("LTP"). In certain non-limiting embodiments the LTP specifically targets lung tissue. "Specifically targets lung tissue" means that when said LTP, linked to a cargo molecule to form a LTP-cargo complex, is injected into a mammal, the LTP-cargo complex is transduced into lung tissue at much higher levels than it is transduced into other tissues, such as, for example, liver, kidney, heart, skeletal muscle, or brain. In certain embodiments the ratio of transduction of a LTP that "specifically targets lung tissue" into lung tissue relative to liver, kidney, heart, skeletal muscle or brain is at least 2:1, at least 3:1, at least 4:1, at least 5:1, at least 6:1, at least 7:1, at least 8:1, at least 9:1, or at least 10:1.

Lung targeting peptides (LTP, SEQ ID NO: 1 or 2) were identified by alanine-scan of the cardiac targeting peptide (CTP, APWHLSSQYSRT, SEQ ID NO:3), described in WO2019226785A1. The LTP peptides, CTP, and other CTP variants are shown in Table 1.

TABLE 1

Peptides of the present disclosure

| SEQ ID NO: | Amino acid sequence |
|---|---|
| 1 | APWHLSAQYSRT (LTP, S7A) |
| 2 | APWHLSSQYSAT (LTP, R11A) |
| 3 | APWHLSSQYSRT (CTP) |
| 4 | APWHLS (CTP-A) |
| 5 | SQYSRT (CTP-B) |
| 6 | AAWHLSSQYSRT (CTP-P2A) |
| 7 | APWALSSQYSRT (H4A) |
| 8 | APWHASSQYSRT (L5A) |
| 9 | APWHLASQYSRT (S6A) |
| 10 | APWHLSSAYSRT (Q8A) |
| 11 | APWHLSSQASRT (Y9A) |
| 12 | APWHLSSQYART (S10A) |
| 13 | APWHLSSQYSRA (T12A) |
| 14 | APAHLSSQYSRT (W3A) |
| 15 | KAPWHLSAQYSRT (LTP, cyclic S7A) |
| 16 | KAPWHLSSQYSAT (LTP, cyclic R11A) |
| 17 | KAPWHLSSQYSRT (cyclic CTP) |

TABLE 1-continued

Peptides of the present disclosure

| SEQ ID NO: | Amino acid sequence |
|---|---|
| 18 | KAPWHLS (cyclic CTP-A) |
| 19 | KSQYSRT (cyclic CTP-B) |
| 20 | KAAWHLSSQYSRT (cyclic CTP-P2A) |
| 21 | KAPWALSSQYSRT (cyclic H4A) |
| 22 | KAPWHASSQYSRT (cyclic L5A) |
| 23 | KAPWHLASQYSRT (cyclic S6A) |
| 24 | KAPWHLSSAYSRT (cyclic Q8A) |
| 25 | KAPWHLSSQASRT (cyclic Y9A) |
| 26 | KAPWHLSSQYART (cyclic S10A) |
| 27 | KAPWHLSSQYSRA (cyclic T12A) |
| 28 | KAPAHLSSQYSRT (cyclic W3A) |

A peptide of Table 1 may be a recombinant or synthetically prepared peptide. In some embodiments, a peptide comprising the amino acid sequence of any one of SEQ ID NOs: 1-14 comprises an N-terminal lysine residue (SEQ ID NOs: 15-28) to generate a cyclic peptide. As used herein, "cyclic peptide" or "cyclized peptide" refers to a peptide comprising the amino acid sequence of any one of SEQ ID NOs: 1-14 with an N-terminal residue (e.g., lysine) suitable for establishing a chemical bond with the C-terminal residue of the amino acid sequence.

In certain embodiments, the LTP of SEQ ID NO: 1 or 2 (or a cyclized version of the peptide) is conjugated to a radionuclide or radioactive moiety, biotin, luciferase, an enzyme, rhodamine, a fluorophore, nanoparticle, microbubbles, liposomes or a luminescent moiety. In certain embodiments, the LTP of SEQ ID NO: 1 or 2 (or a cyclized version of the peptide) is conjugated to a radionuclide or radioactive moiety, biotin, luciferase, an enzyme, rhodamine, a fluorophore, nanoparticle, microbubbles, liposomes or a luminescent moiety. In certain embodiments, the LTP of SEQ ID NO: 1 or 2 (or a cyclized version of the peptide) is conjugated to a radionuclide or radioactive moiety, biotin, luciferase, an enzyme, rhodamine, a fluorophore, nanoparticle, microbubbles, liposomes or a luminescent moiety, via an ester linkage. In certain embodiments, a cyclic peptide of the present application is conjugated to a radionuclide or radioactive moiety, biotin, luciferase, an enzyme, rhodamine, a fluorophore, nanoparticle, microbubbles, liposomes or a luminescent moiety. In certain embodiments, the cyclic peptide of the present application is conjugated to a radionuclide or radioactive moiety, biotin, luciferase, an enzyme, rhodamine, a fluorophore, nanoparticle, microbubbles, liposomes or a luminescent moiety. In certain embodiments, the cyclic peptide of the present application is conjugated to a radionuclide or radioactive moiety, biotin, luciferase, an enzyme, rhodamine, a fluorophore, nanoparticle, microbubbles, liposomes or a luminescent moiety, via an ester linkage.

In another aspect, the present disclosure provides a method of imaging or detecting a tissue, comprising administering an effective amount of a composition comprising the detectable agent-conjugated LTP of SEQ ID NO: 1 or 2 (or a cyclized version of the peptide) to a subject; exposing the subject to conditions conducive to detection of the LTP conjugate; and obtaining an image. In another aspect, the present disclosure provides a method of imaging or detecting a tissue, comprising administering an effective amount of a composition comprising the detectable agent-conjugated cyclic peptide to a subject; exposing the subject to conditions conducive to detection of the LTP conjugate; and obtaining an image.

In another aspect, the present disclosure provides a LTP of SEQ ID NO: 1 or 2 (or a cyclized version of the peptide) formulated as a delivery vehicle/agent. In certain embodiments, the LTP of SEQ ID NO: 1 or 2 (or a cyclized version of the peptide) is conjugated to a drug or therapeutic, a nanoparticle, a peptide, a protein, a nucleic acid, or a detectable agent. In certain embodiments, the LTP of SEQ ID NO: 1 or 2 is conjugated to a drug or therapeutic, a nanoparticle, a peptide, a protein, or a detectable agent via an ester linkage. In another aspect, the present disclosure provides the cyclic peptide formulated as a delivery vehicle/ agent. In certain embodiments, the cyclic peptide is conjugated to a drug or therapeutic, a nanoparticle, a peptide, a protein, a nucleic acid, or a detectable agent. In certain embodiments, the cyclic peptide is conjugated to a drug or therapeutic, a nanoparticle, a peptide, a protein, or a detectable agent via an ester linkage.

In certain embodiments, the LTP of SEQ ID NO: 1 or 2 (or a cyclized version of the peptide) is linked/conjugated to the drug or therapeutic, the nanoparticle, the peptide, the protein, the nucleic acid, or the detectable agent via an ester linkage, disulfide or protease sensitive linkers. In certain embodiments, the LTP of SEQ ID NO: 1 or 2 (or a cyclized version of the peptide) is linked/conjugated to the drug or therapeutic, the nanoparticle, the peptide, the protein, the nucleic acid, or the detectable agent via an ester linkage, disulfide, or protease sensitive linkers. In certain embodiments, the LTP of SEQ ID NO: 1 or 2 (or a cyclized version of the peptide) is linked/conjugated to a nucleic acid therapeutic, e.g., an siRNA, via a disulfide linkage. In certain embodiments, the cyclic peptide is linked/conjugated to the drug or therapeutic, the nanoparticle, the peptide, the protein, the nucleic acid, or the detectable agent via an ester linkage, disulfide or protease sensitive linkers. In certain embodiments, the cyclic peptide is linked/conjugated to the drug or therapeutic, the nanoparticle, the peptide, the protein, the nucleic acid, or the detectable agent via an ester linkage, disulfide, or protease sensitive linkers. In certain embodiments, the cyclic peptide is linked/conjugated to a nucleic acid therapeutic, e.g. an siRNA, via a disulfide linkage.

In another aspect, the present disclosure provides a method of treating lung tissue or a lung condition in a subject in need thereof, comprising administering to the subject a therapeutically effective amount of a composition comprising the LTP of SEQ ID NO: 1 or 2 (or a cyclized version of the peptide). In certain embodiments, the LTP of SEQ ID NO: 1 or 2 (or a cyclized version of the peptide) is used in a method of treating lung tissue or a lung condition in a subject in need thereof.

In another aspect, the present disclosure provides a method of treating cardiac tissue or a cardiac condition in a subject in need thereof, comprising administering to the subject a therapeutically effective amount of a composition comprising a cyclic peptide. In certain embodiments, the cyclic peptide is used in a method of treating cardiac tissue or a cardiac condition in a subject in need thereof.

In another aspect, the present disclosure provides a method of introducing a cargo into a lung epithelial cell comprising administering, to the lung epithelial cell, an amount of a complex comprising the LTP of SEQ ID NO: 1 or 2 (or a cyclized version of the peptide) linked to a cargo effective to introduce the cargo into the epithelial cell. In certain embodiments, the cargo comprises a radioisotope, fluorescent marker, gadolinium marker, luciferase marker, microsphere or nanoparticle. In certain embodiments, the LTP of SEQ ID NO: 1 or 2 is conjugated to the cargo via an ester linkage. In another aspect, the present disclosure provides a method of introducing a cargo into a lung epithelial cell comprising administering, to a cell (e.g., cardiac muscle cell, or lung epithelial cell) an amount of a complex comprising the cyclic peptide linked to a cargo effective to introduce the cargo into the cell. In certain embodiments, the cargo comprises a radioisotope, fluorescent marker, gadolinium marker, luciferase marker, microsphere or nanoparticle. In certain embodiments, the cyclic peptide is conjugated to the cargo via an ester linkage.

In another aspect, the present disclosure provides a method of treating a human subject suffering from chronic obstructive pulmonary disease (COPD), comprising introducing a cargo into a lung cell of the human subject comprising administering, to the human subject, a therapeutically effective amount of a complex comprising the LTP of SEQ ID NO: 1 or 2 (or a cyclized version of the peptide) linked to a cargo, where the cargo inhibits cell death, lengthens subject survival, or a combination thereof. In certain embodiments, the cargo is selected from an NF-κB inhibitor, NBD peptide, heme oxygenase, an antioxidant, iNOS, superoxide dismutase, catalase, glutathione peroxidase, Mitotempo, a TGFβ inhibitor, VEGF, FGF-1, FGF-2, sonic hedgehog protein, HGF and an IAP. In certain embodiments, the LTP of SEQ ID NO: 1 or 2 (or a cyclized version of the peptide) is used in a method of treating a human subject suffering from chronic obstructive pulmonary disease (COPD). In certain embodiments, the LTP of SEQ ID NO: 1 or 2 is conjugated to the cargo via an ester linkage.

In some embodiments, the peptide of the present disclosure (e.g., LTP) is a linear peptide. In some embodiments, the peptide of the present disclosure (e.g., LTP) is a cyclic peptide. Methods of synthesizing cyclic peptides are known in the art (e.g., Chow et al. (2019), Ligation Technologies for the Synthesis of Cyclic Peptides. *Chem Rev.* 119(17):9971-10001, Choi et al. (2020), Recent Trends in Cyclic Peptides as Therapeutic Agents and Biochemical Tools. *Biomol Ther.* 28(1):18-24, and US 2019/0300571).

A cyclic peptide, e.g. a cyclic LTP, may be circularized by connecting (e.g., connecting by a chemical bond) the amino and carboxyl termini of the peptide. In some embodiments, an N-terminal lysine residue is added to a peptide described in the present disclosure (e.g., SEQ ID NOs: 1-14). In some embodiments, an N-terminal lysine residue is added to an LTP described in the present disclosure (e.g., R11A or S7A, SEQ ID NO: 1 or 2). In some embodiments, an N-terminal lysine residue is added to a CTP variant described in the present disclosure (e.g., any one of SEQ ID NOs: 3-14). In some embodiments, a cyclic peptide comprises the amino acid sequence of any one of SEQ ID NOs: 15-28. In some embodiments, a cyclic LTP comprises the amino acid sequence of SEQ ID NO: 15 or 16. In some embodiments, a cyclic peptide comprises the amino acid sequence of any one of SEQ ID NOs: 17-28. In some embodiments, the alpha-amino group of the N-terminal lysine is connected to the C-terminus of the peptide sequence. In some embodiments, the epsilon amino group of the lysine residue is further connected, e.g., conjugated, to a therapeutic cargo. In certain embodiments, the epsilon amino group of the lysine residue is further connected, e.g., conjugated, to a fluorescent detector. In certain embodiments, the epsilon amino group of the lysine residue is further connected, e.g., conjugated, to a nucleic acid, e.g. an siRNA. In certain embodiments, the epsilon amino group of the lysine residue is connected to a linker, e.g., a thiol linker, e.g., 3-mercapto-proprionic acid, and said linker is connected, e.g., conjugated, to a nucleic acid, e.g. an siRNA. In certain embodiments, the epsilon amino group of the lysine residue is connected to a suitable linker for connecting, e.g., conjugating, another therapeutic cargo, depending on the type of therapeutic application of interest for the conjugation. Examples of suitable linkers and methods for determining suitable linkers for connecting to a cyclic peptide are found, for example, in He et al. (2019), Peptide Conjugates with Small Molecules Designed to Enhance Efficacy and Safety. *Molecules*. 24(1855), and Vrettos et al. (2018), On the design principles of peptide—drug conjugates for targeted drug delivery to the malignant tumor site. *J Org Chem*. 14:930-954. Suitable linkers include, without limitation, disulfides, thioethers, imides, oximes, hydrazones, esters, amides, and as enzyme-hydrolyzable Valine-citrulline linkers. In some embodiments, the therapeutic cargo is added to the LTP after cyclization.

In certain embodiments, a cyclic peptide of the present disclosure, e.g., cyclic LTP, demonstrates enhanced stability (e.g., stability in a sample) relative to said LTP in linear form. In certain embodiments, a cyclic peptide of the present disclosure, e.g., cyclic LTP, demonstrates enhanced biological activity (e.g., increased delivery of therapeutic cargo, e.g., increased delivery of a fluorescent detector) relative to said peptide in linear form.

In another aspect, the present disclosure provides a method of treating a human subject suffering from a lung disease or disorder, comprising introducing a cargo into a lung epithelial cell of the human subject comprising administering, to the human subject, a therapeutically effective amount of a complex comprising the LTP of SEQ ID NO: 1 or 2 linked to a cargo, wherein the cargo inhibits cell death, lengthens subject survival, or a combination thereof. In certain embodiments, the cargo is selected from an NF-κB inhibitor, NBD peptide, heme oxygenase, an antioxidant, iNOS, superoxide dismutase, catalase, glutathione peroxidase, Mitotempo, a TGFβ inhibitor, VEGF, FGF-1, FGF-2, sonic hedgehog protein, HGF and an IAP. In certain embodiments, the LTP of SEQ ID NO: 1 or 2 is linked/conjugated to the cargo via an ester linkage.

In certain embodiments a cyclic peptide comprising is linked to a moiety having antiarrhythmic properties, for example amiodarone, and used in a method of treating cardiac tissue or a cardiac condition in a subject in need thereof. In certain embodiments a cyclic peptide comprising an amino acid sequence of SEQ ID NO: 17 is linked to a moiety having antiarrhythmic properties, for example amiodarone, and used in a method of treating cardiac tissue or a cardiac condition in a subject in need thereof. In certain embodiments a cyclic peptide comprising an amino acid sequence of SEQ ID NO: 18 is linked to a moiety having antiarrhythmic properties, for example amiodarone, and used in a method of treating cardiac tissue or a cardiac condition in a subject in need thereof. In certain embodiments a cyclic peptide comprising an amino acid sequence of SEQ ID NO: 19 is linked to a moiety having antiarrhythmic properties, for example amiodarone, and used in a method of treating cardiac tissue or a cardiac condition in a subject in need thereof. In certain embodiments, the cardiac condition is an atrial arrhythmia, for example, atrial fibrillation. In certain embodiments, the cardiac condition is a ventricular arrhythmia, for example, ventricular tachycardia.

II. Cargo

In some embodiments, the LTP of any one of SEQ ID NOs: 1 or 2 (or a cyclized version of the peptide), is linked with a cargo molecule to form a complex, optionally via a linker molecule or molecules. In some embodiments, a cyclic peptide of the present application is linked with a cargo molecule to form a complex, optionally via a linker molecule or molecules. The cargo molecule may be a protein (including a glycoprotein), a nucleic acid, a carbohydrate, a lipid, a nanoparticle, or a combination thereof. In some embodiments, the cargo comprises a detectable agent. Examples of detectable agents include, but are not limited to, a radioisotope, a fluorescent marker (e.g., a fluorophore, e.g., rhodamine), gadolinium, an enzyme (e.g., luciferase), microspheres, radionuclides or radioactive moieties, biotin, an nanoparticle, microbubbles, liposomes, or a luminescent moiety. In some embodiments, the cargo molecule is an active pharmaceutical ingredient.

In certain non-limiting embodiments, the cargo comprises a lipid-based structure. Examples of lipid-based structures include, but are not limited to, a lipid-based nanoparticle, a liposome, a micelle, an exosome, a vesicle, an extracellular vesicle, a cell, or a tissue. In one embodiment, the cargo is a liposome.

In certain non-limiting embodiments, the cargo is a peptide, a protein, a peptide conjugate, or a protein-conjugate. In certain non-limiting embodiments, the protein is selected from the group consisting of a cytokine, a growth factor, an enzyme, an ion channel, and an anti-inflammatory protein. In certain non-limiting embodiments, the peptide-conjugate is a peptide-nucleic acid conjugate.

In certain non-limiting embodiments, the cargo is an antioxidant.

In certain non-limiting embodiments, the cargo comprises a virus or virus-like particles.

In certain non-limiting embodiments, the cargo is a nucleic acid. Non-limiting examples of such nucleic acid include DNA, RNA, antisense RNA, interfering RNA (for example, small interfering RNA (siRNA), small nuclear RNA (snRNA), non-coding RNA), microRNA (miRNA), messenger RNA (mRNA), catalytic RNA, catalytic DNA, DNA origami, oligonucleotides, nucleoside analogs, poly-nucleic acid decoys, aptamers, plasmid DNA/plasmids, genes, and gene therapy agents. In another set of non-limiting embodiments, the cargo is a vector comprising a therapeutic gene, for example an adenovirus vector or a lentivirus vector.

In certain non-limiting embodiments, the cargo is a small molecule. In some embodiments, the small molecule has ROS scavenging properties. In some embodiments, the small molecule is a bronchodilator, e.g., β2-agonists, anti-cholinergic agents, and methylxanthines. In some embodiments, the small molecule is a corticosteroid, e.g., fluticasone, budesonide, mometasone, beclomethasone, and ciclesonide. In some embodiments, the small molecule is a phosphodiesterase-4 inhibitor. In some embodiments, the small molecule is an antibiotic. In some embodiments, the small molecule is an anti-cancer agent, e.g., a chemotherapeutic.

In certain non-limiting embodiments, the LTP linked to a therapeutic moiety specifically targets lung tissue. "Specifically targets lung tissue" means that when said LTP conjugate, linked to a second peptide sequence, a protein, or a small molecule to form a conjugated protein, is injected into a mammal, the conjugated protein is transduced into lung tissue at much higher levels than it is transduced into other tissues, such as, for example, liver, kidney, heart, skeletal muscle, or brain.

In certain non-limiting embodiments, the LTP of SEQ NO: 1 or 2 (or a cyclized version of the peptide) is comprised of (L) amino acids. In certain non-limiting embodiments, the LTP of SEQ ID NO: 1 or 2 (or a cyclized version of the peptide) is comprised of (D) amino acids. In certain non-limiting embodiments, the LTP of SEQ ID NO: 1 or 2 (or a cyclized version of the peptide) is comprised of (L) and (D) amino acids.

In embodiments, the invention provides a peptide that includes a twelve amino acid Lung-specific Targeting-Peptide (LTP12aa) comprising the sequence of SEQ ID NO: 1 or 2 linked/conjugated to a second peptide sequence, a protein, or a small molecule that has reactive oxygen species (ROS) scavenging properties. In some embodiments, the second peptide sequence, protein, or small molecule is conjugated upstream of the N-terminus of the LTP peptide. In some embodiments the peptide can include an ester linkage between the LTP and the second peptide sequence, protein, or small molecule, and the ester linkage can only be cleaved by an intracellular esterase. Examples of peptide sequences, proteins, and small molecules with ROS scavenging properties include, but are not limited to, hemeoxygenase 1, Mitotempo, resveratrol, N-acetyl-cysteine, N-tert-butyl-α-phenylnitrone, and 4-hydroxy-2,2,6,6-tetramethylpiperidine-1-oxyl.

In some embodiments, the peptide is optionally further labelled at both the C- and N-termini. For example, in some embodiments, the peptide is labelled with a green fluorescent moiety, for example, 6-carboxyfluorescein, and a red fluorescent moiety, for example, Cy5.5. For example, in some embodiments, the peptide is labelled with a green fluorescent moiety at its N-terminus and a red fluorescent moiety at its C-terminus. In some embodiments, the peptide is labelled with a red fluorescent moiety at its N-terminus and a green fluorescent moiety at its C-terminus.

The present disclosure is based, in part, on directly delivering an ROS scavenging peptide (for example, SS-31 or SS-02), protein, or small molecule to the lung using LTP to target peptide delivery to cells of the lung, for example, lung epithelial cells. ROS scavenging peptides include Szeto-Schiller (SS) peptides (for example, SS-01, SS-02, and SS-31), which contain alternating aromatic and basic amino acids, including tyrosine or dimethyltyrosine, and which are highly cell permeable. SS peptides are described in Szeto HH, (2006) "Cell-permeable, Mitochondrial-targeted, Peptide Antioxidants" The AAPS Journal 8(2):E277-E283, the entire contents of which are incorporated herein by reference. In some embodiments the invention provides a method of delivering an ROS scavenging peptide (for example, SS-31 or SS-02), protein, or small molecule to cells of a subject's lung, for example, a subject's lung epithelial cells. In some embodiments, the subject is a mammal, for example, a primate, for example, a human.

Thus, in some embodiments the invention provides a method of delivering an ROS scavenging peptide (for example, SS-31 or SS-02), protein, or small molecule to cells of a human subject's lung, for example, a human subject's lung epithelial cells. In some embodiments the invention provides a method of delivering an ROS scavenging peptide (for example, SS-31 or SS-02), protein, or small molecule to cells of a subject's lung, for example, a subject's lung epithelial cells, by administering a peptide that includes LTP linked/conjugated to an ROS scavenging peptide (for example, SS-31 or SS-02), protein, or small molecule, for example, by an ester linkage, to the subject. In some embodiments, the peptide can be introduced by means of a cell or a virus that includes a nucleic acid encoding a LTP linked/conjugated peptide sequence.

In some aspects, the invention provides a method of scavenging ROS in cell culture by exposing a cell culture (for example, cells and/or cell culture media) to a peptide that includes LTP linked/conjugated to a second peptide sequence, a protein, or a small molecule with ROS scavenging properties. For example, in some embodiments, the invention provides a method of scavenging ROS in cell culture by exposing a cell culture to a peptide that includes LTP linked/conjugated to SS-31 (SS-LTP-31) or LTP conjugated to SS-02 (SS-LTP-02). In some embodiments, exposing a cell culture to a peptide that includes LTP linked/conjugated to a second peptide sequence, a protein, or a small molecule with ROS scavenging properties is achieved by expressing the peptide in one or more cells in the cell culture and/or by viral infection.

In certain embodiments, the invention provides formulating a peptide composition, for example, an SS-LTP composition, in a stable formulation for delivery to cells in vitro as well as to animals via intravenous perfusion. In certain embodiments, the invention provides formulating a peptide composition, for example, an SS-LTP composition, in a stable formulation for delivery to cells in vitro as well as to animals via the inhalational route, including nebulization. In certain embodiments, the invention provides delivering the formulated composition to a mammalian lung epithelial cell and monitoring for cellular toxicity by performing a cell viability assay. In certain embodiments, the invention provides delivering a peptide, for example, an SS-LTP, to a mammalian lung epithelial cell line challenged with oxidative stress (for example, a lung epithelial cell line challenged with oxidative stress using hydrogen peroxide) as a stressor. In some embodiments, the invention also includes assessing mitochondrial function at baseline, under stress with H2O2, and in cells treated with an SS-LTP prior to challenge with H2O2 using a Seahorse analyzer (Agilent Technologies, Inc., Santa Clara, CA, USA). In certain embodiments, the invention provides delivering an SS-LTP to a mammal having chronic obstructive pulmonary disease (COPD). In some embodiments, the invention also includes observing one or more mucociliary parameters, for example, mucociliary clearance (MCC), goblet cell density, degree of ciliation in vivo, ciliary beat frequency, cilia length, cytokine levels, mitochondrial morphology/function, and inflammatory infiltrates, to assess efficacy at various time points before, during, and/or after delivery and/or treatment. In certain embodiments, the invention provides administering an SS-LTP intravenously weekly, for example, for 6-12 weeks, and assessing for hepatic, renal, CNS, and/or lung toxicity using blood chemistry and/or histology.

In certain embodiments, the invention provides formulating a peptide composition that includes LTP linked/conjugated to a second peptide sequence, a protein, or a small molecule with ROS scavenging properties, in a stable formulation for delivery to cells in vitro as well as to animals via intravenous perfusion. In certain embodiments, the invention provides delivering the formulated composition to a mammalian lung epithelial cell and monitoring for cellular toxicity by performing a cell viability assay. In certain embodiments, the invention provides delivering a peptide that includes LTP linked/conjugated to a second peptide sequence, a protein, or a small molecule with ROS scavenging properties, to a mammalian lung epithelial cell line challenged with oxidative stress (for example, a lung epithelial cell line challenged with oxidative stress using hydrogen peroxide) as a stressor. In some embodiments, the invention also includes assessing mitochondrial function at baseline, under stress with $H_2O_2$, and in cells treated with the peptide prior to challenge with $H_2O_2$, using Seahorse. In certain embodiments, the invention provides delivering a peptide that includes LTP linked/conjugated to a second peptide sequence, a protein, or a small molecule with ROS scavenging properties to a mammal having chronic obstructive pulmonary disease (COPD). In some embodiments, the invention also includes observing one or more mucociliary parameters, for example, mucociliary clearance (MCC), goblet cell density, degree of ciliation in vivo, ciliary beat frequency, cilia length, cytokine levels, mitochondrial morphology/function, and inflammatory infiltrates. In certain embodiments, the invention provides administering a peptide that includes LTP linked/conjugated to a second peptide sequence, a protein, or a small molecule with ROS scavenging properties intravenously weekly, for example, for 6-12 weeks, and assessing for hepatic, renal, CNS, and/or lung toxicity using blood chemistry and/or histology.

In certain embodiments, one specific non-limiting example of a cargo is extracellular superoxide dismutase. Further specific non-limiting examples of cargo include Cu/Zn-SOD, Mn-SOD, catalase, Mitotempo, and glutathione peroxidase. One specific non-limiting example of cargo is transforming growth factor beta ("TGFβ") type II receptor (Ad.CAG-s TGFβII), a competitive inhibitor of TGFβ. One specific non-limiting example of cargo is VEGF (vascular endothelial growth factor), for example human VEGF. One specific non-limiting example of cargo is fibroblast growth factor (FGF), for example human FGF-1 or FGF-2. One specific non-limiting example of cargo is hepatocyte growth factor ("HGF"). One set of non-limiting examples of cargo is an apoptosis inhibitor, such as one of the so-called inhibitors of apoptosis ("IAPs"), for example, the human IAPs c-IAP1, c-IAP2, and XIAP. One specific non-limiting example of cargo is Sonic Hedgehog protein. One specific non-limiting example of cargo is glucocerebrosidase, for example human glucocerebrosidase used for treatment in Gaucher's disease. One specific non-limiting example of cargo is an RNA molecule, e.g., an siRNA, a miRNA, or an antisense RNA, that inhibits expression of TGFβ.

In another set of non-limiting embodiments, the cargo is a nanoparticle or a microsphere containing a diagnostic or therapeutic agent. In another set of non-limiting embodiments, the cargo is a vector comprising a therapeutic gene, for example an adenovirus vector or a lentivirus vector. In another set of non-limiting embodiments, the cargo is a detectable compound for analysis of uptake in viable lung cells versus non-viable cells following pulmonary injury. Non-limiting examples of detectable compounds include fluorodeoxyglucose, technetium-99 or other radioisotope-labelled cargo, fluorescent markers, gadolinium markers, etc.

III. Linkers

The LTP of any one of SEQ ID NOs: 1 or 2 (or a cyclized version of the peptide), and the cargo are linked covalently or non-covalently, optionally via one or more linker molecules. Where the bond is a covalent bond, LTP of any one of SEQ ID NOs: 1 or 2 (or a cyclized version of the peptide) and cargo, optionally with a linker(s) between, may be joined via one or more peptide bond, thioester bond, thioether bond, carbamate bond, etc., which can be created according to methods generally and well known in the art.

In certain embodiments, the linker may comprise a cleavage site that may, upon enzymatic or chemical cleavage, release the LTP of any one of SEQ ID NOs: 1 or 2 (or a cyclized version of the peptide), from its cargo. In certain non-limiting embodiments, the linker may be a ligand pair. As one specific example, the linker may be an avidin/biotin pair.

Accordingly, the invention provides for a complex comprising a LTP of any one of SEQ ID NOs: 1 or 2 (or a cyclized version of the peptide), linked to a cargo. The invention also provides for a complex comprising a cyclic protein linked to a cargo. The complex may comprise additional elements. For example, the LTP of any one of SEQ ID NOs: 1 or 2 (or a cyclized version of the peptide), and/or cargo may be conjugated to one or more additional molecule that improves delivery or stability. As one non-limiting example, the LTP of any one of SEQ ID NOs: 1 or 2 (or a cyclized version of the peptide), and/or cargo may be PEGylated. As another non-limiting example, the cargo may be linked to a nuclear transport peptide. As another non-limiting example, the cargo may be linked to a detectable compound.

IV. Methods of Use

In one aspect, the present disclosure provides a method of treating a human subject suffering from lung disease or disorder, comprising introducing into the lung tissue of the human subject a compound comprising a recombinant and isolated Lung-specific Targeting-Peptide (LTP) of the sequence of SEQ ID NO: 1 or 2 (or a cyclized version of the peptide) linked to a drug or therapeutic, or a formulation thereof. In some embodiments, the subject suffers from a pulmonary disease, e.g., chronic obstructive pulmonary disease (COPD), emphysema, chronic bronchitis, acute bronchitis, pneumonia, tuberculosis, pulmonary edema, acute respiratory distress syndrome (ARDS), pneumoconiosis, interstitial lung disease (ILD), asthma, primary ciliary dyskinesia (PCD), cystic fibrosis (CF), bronchogenic carcinoma, small cell lung cancer (SCLC), and non-small cell lung cancer (NSCLC) (e.g., adenocarcinoma, squamous cell carcinoma, large-cell undifferentiated carcinoma, salivary gland-type lung carcinoma, and mesothelioma). In certain embodiments, the present disclosure provides a method of treating a human subject suffering from COPD, comprising introducing a cargo into a lung cell of the human subject by administering to the human subject an LTP comprising the sequence of SEQ ID NO: 1 or SEQ ID NO: 2 (or a cyclized version of the peptide) conjugated to a therapeutic agent.

In certain embodiments, the present disclosure provides a method of treating a human subject suffering from pneumonia, comprising introducing a cargo into a lung cell of the human subject by administering to the human subject an LTP comprising the sequence of SEQ ID NO: 1 or SEQ ID NO: 2 (or a cyclized version of the peptide) conjugated to a therapeutic agent.

In certain embodiments, the present disclosure provides a method of treating a human subject suffering from asthma, comprising introducing a cargo into a lung cell of the human subject by administering to the human subject an LTP comprising the sequence of SEQ ID NO: 1 or SEQ ID NO: 2 (or a cyclized version of the peptide) conjugated to a therapeutic agent.

In certain embodiments, the present disclosure provides a method of treating a human subject suffering from CF, comprising introducing a cargo into a lung cell of the human subject by administering to the human subject an LTP comprising the sequence of SEQ ID NO: 1 or SEQ ID NO: 2 (or a cyclized version of the peptide) conjugated to a therapeutic agent.

In certain embodiments, the present disclosure provides a method of treating a human subject suffering from lung cancer, comprising introducing a cargo into a lung cell of the human subject by administering to the human subject an LTP comprising the sequence of SEQ ID NO: 1 or SEQ ID NO: 2 (or a cyclized version of the peptide) conjugated to a therapeutic agent.

In another aspect, the present disclosure provides a method of growing and/or re-cilliating tracheal epithelial cells (MTCs) and/or nasal epithelial cells of a mammal, the method comprising introducing into the lung tissue of the human subject a compound comprising a recombinant and isolated Lung-specific Targeting-Peptide (LTP) of the sequence of SEQ ID NO: 1 or 2 (or a cyclized version of the peptide) linked to a drug or therapeutic (for example, in some embodiments, the drug or therapeutic is an ROS scavenger, or a γ-secretase or Notch inhibitor), or a formulation thereof.

V. Pharmaceutical Compositions

For therapeutic use, an LTP of SEQ ID NO: 1 or SEQ ID NO: 2 (or a cyclized version of the peptide) linked to a therapeutic agent described herein preferably is combined with a pharmaceutically acceptable carrier. In some embodiments, for therapeutic use, a cyclic peptide linked to a therapeutic agent described herein preferably is combined with a pharmaceutically acceptable carrier. The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein refers to buffers, carriers, and excipients suitable for use in contact with the tissues of human beings and animals without excessive toxicity, irritation, allergic response, or other problem or complication, commensurate with a reasonable benefit/risk ratio. Pharmaceutically acceptable carriers include any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, e.g., Martin, Remington's Pharmaceutical Sciences, 15th Ed., Mack Publ. Co., Easton, PA [1975]. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Where the LTP of SEQ ID NO: 1 or SEQ ID NO: 2 (or a cyclized version of the peptide), in complex with a cargo is administered to a subject, the subject may be a human subject or a non-human subject, such as a primate, a companion animal (e.g., dog, cat, horse) a laboratory animal (e.g., mouse, rat, rabbit or guinea pig) or a farm animal (cow, goat, etc.). Where cyclic peptide, in complex with a cargo is administered to a subject, the subject may be a human subject or a non-human subject, such as a primate, a companion animal (e.g., dog, cat, horse) a laboratory animal (e.g., mouse, rat, rabbit or guinea pig) or a farm animal (cow, goat, etc.).

The LTP of SEQ ID NO: 1 or SEQ ID NO: 2 (or a cyclized version of the peptide), in complex with a cargo, may be administered by any route including, but not limited to intravenous, inhalational, intraarterial, intraperitoneal, subcutaneous, oral, rectal, etc. The cyclic peptide, in complex with a cargo, may be administered by any route including, but not limited to intravenous, inhalational, intraarterial, intraperitoneal, subcutaneous, oral, rectal, etc.

The present disclosure provides for pharmaceutical compositions comprising an LTP of SEQ ID NO: 1 or SEQ ID NO: 2 (or a cyclized version of the peptide), in complex with a cargo, and a suitable pharmaceutical carrier, for example, water, physiologic saline. The present disclosure provides for pharmaceutical compositions comprising a cyclic peptide, in complex with a cargo, and a suitable pharmaceutical carrier, for example, water, physiologic saline.

VI. Combination Treatment and Formulations

In certain embodiments, the LTP of SEQ ID NO: 1 or SEQ ID NO: 2 (or a cyclized version of the peptide) linked to a therapeutic agent can be formulated, or co-administered (either at the same time or sequentially), for example, by an enteral route (e.g., orally), with a pH increasing agent, for example, a protein pump inhibitor (PPI), to enhance the stability of the LTP of SEQ ID NO: 1 or SEQ ID NO: 2, for example, e.g., in an acidic environment, e.g., in the gastrointestinal tract.

In certain embodiments, the cyclic peptide of the present disclosure linked to a therapeutic agent can be formulated, or co-administered (either at the same time or sequentially), for example, by an enteral route (e.g., orally), with a pH increasing agent, for example, a protein pump inhibitor (PPI), to enhance the stability of the cyclic peptide of the present disclosure, for example, e.g., in an acidic environment, e.g., in the gastrointestinal tract.

Proton pump inhibitors are a group of drugs whose main action is pronounced and long-lasting reduction of gastric acid production. Proton pump inhibitors act by blocking the hydrogen/potassium adenosine triphosphatase enzyme system (the H+/K+ ATPase, or more commonly just gastric proton pump) of the gastric parietal cell. The proton pump is the terminal stage in gastric acid secretion, being directly responsible for secreting H+ ions into the gastric lumen, making it an ideal target for inhibiting acid secretion. Examples of proton pump inhibitors include: Omeprazole (brand names: LOSEC®, PRILOSEC®, ZEGERID®); Lansoprazole (brand names PREVACID®, ZOTON®, INHIBI-TOL®); Esomeprazole (brand names NEXIUM®); and Pantoprazole (brand names: PROTONIX®, SOMAC®, PANTOLOC®).

Pharmaceutical compositions containing an LTP of SEQ ID NO: 1 or SEQ ID NO: 2 (or a cyclized version of the peptide), or a cyclic peptide described herein, linked to a therapeutic agent disclosed herein can be presented in a dosage unit form and can be prepared by any suitable method. A pharmaceutical composition should be formulated to be compatible with its intended route of administration. The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form will depend upon the intended mode of administration and therapeutic application.

Although the compositions preferably are formulated for administration enterally (for example, orally), such compositions can be administered by a parenteral mode (e.g., inhalational, or intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and infrasternal injection and infusion, and inhalational.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Depending upon the mode of administration, for example, by parenteral administration, it may be desirable to produce a pharmaceutical formulation that is sterile. Sterilization can be accomplished by any suitable method, e.g., filtration through sterile filtration membranes. Where the composition is lyophilized, filter sterilization can be conducted prior to or following lyophilization and reconstitution.

In certain embodiments, a disclosed composition comprises a polyionic reagent which may, e.g., coat the LTP of SEQ ID NO: 1 or SEQ ID NO: 2 linked to a therapeutic agent, i.e., the composition comprises a polyionic coating. Exemplary polyionic reagents include PSS (poly(Sodium 4-styrenesulfonate), PAA (poly Acrylic acid sodium salt), PMG (poly(methylene-co-guanidine) hydrochloride), DS (dextran sulfate), PMA (poly(methyl acrylate)), or PVS (polyvinylsiloxane).

Lyophilized Formulation

The lyophilized formulation for use in a method of treatment of the present disclosure includes a peptide of the present disclosure, e.g., the Lung-specific Targeting-Peptide (LTP) (e.g., SEQ ID NO: 1 or SEQ ID NO: 2 (or a cyclized version of the peptide)) linked to a drug or therapeutic agent and a lyoprotectant. In certain embodiments, the lyophilized formulation for use in a method of treatment of the present disclosure includes a peptide of the present disclosure, e.g., the LTP of SEQ ID NO: 1 (or a cyclized version of the peptide) linked to a drug or therapeutic and a lyoprotectant. In certain embodiments, the lyophilized formulation for use in a method of treatment of the present disclosure includes a peptide of the present disclosure, e.g., the LTP of SEQ ID NO: 2 (or a cyclized version of the peptide) linked to a drug or therapeutic and a lyoprotectant. In certain embodiments, the lyoprotectant may be sugar, e.g., disaccharides. In certain embodiments, the lyoprotectant may be sucrose or maltose. In certain embodiments, the lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5.

In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide.

Before lyophilization, the pH of the solution containing the protein of the present disclosure may be adjusted between about 6 to about 8. In certain embodiments, the pH range for the lyophilized drug product may be from about 7 to about 8.

In certain embodiments, a salt or buffer components may be added in an amount of about 10 mM—about 200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counter-ion.

In certain embodiments, a "bulking agent" may be added. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the present disclosure may contain such bulking agents.

A preservative may be optionally added to the formulations herein to reduce bacterial action. The addition of a preservative may, for example, facilitate the production of a multi-use (multiple-dose) formulation.

In certain embodiments, the lyophilized drug product for use in a method of treatment of the present disclosure may be constituted with an aqueous carrier. The aqueous carrier of interest herein is one which is pharmaceutically acceptable (e.g., safe and non-toxic for administration to a human) and is useful for the preparation of a liquid formulation, after lyophilization. Illustrative diluents include sterile water for injection (SWFI), bacteriostatic water for injection (BWFI), a pH buffered solution (e.g., phosphate-buffered saline), sterile saline solution, Ringer's solution or dextrose solution.

In certain embodiments, the lyophilized drug product of the current disclosure is reconstituted with either Sterile Water for Injection, USP (SWFI) or 0.9% Sodium Chloride Injection, USP. During reconstitution, the lyophilized powder dissolves into a solution.

In certain embodiments, the lyophilized protein product of the instant disclosure is constituted to about 4.5 mL water for injection and diluted with 0.9% saline solution (sodium chloride solution).

Liquid Formulation

In embodiments, the Lung-specific Targeting-Peptide (LTP) (e.g., SEQ ID NO: 1 or SEQ ID NO: 2 (or a cyclized version of the peptide)) linked to a drug or therapeutic agent of the present disclosure is formulated as a liquid formulation for use in a method of treatment described herein. In some embodiments, a cyclic peptide of the present disclosure is linked to a drug or therapeutic agent of the present disclosure is formulated as a liquid formulation for use in a method of treatment described herein. The liquid formulation may be presented at a 10 mg/mL concentration in either a USP/Ph Eur type I 50R vial closed with a rubber stopper and sealed with an aluminum crimp seal closure. The stopper may be made of elastomer complying with USP and Ph Eur. In certain embodiments vials may be filled with an effective amount of the LTP conjugated to a drug or therapeutic solution in order to allow an extractable volume. In certain embodiments, the liquid formulation may be diluted with 0.9% saline solution.

In certain embodiments, the liquid formulation for use in a method of the disclosure may be prepared as a solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative.

In certain embodiments, the pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

In addition to aggregation, deamidation is a common product variant of peptides and proteins that may occur during fermentation, harvest/cell clarification, purification, drug substance/drug product storage and during sample analysis. Deamidation is the loss of $NH_3$ from a protein forming a succinimide intermediate that can undergo hydrolysis. The succinimide intermediate results in a 17 unit mass decrease of the parent peptide. The subsequent hydrolysis results in an 18 unit mass increase. Isolation of the succinimide intermediate is difficult due to instability under aqueous conditions. As such, deamidation is typically detectable as 1 unit mass increase. Deamidation of an asparagine results in either aspartic or isoaspartic acid. The parameters affecting the rate of deamidation include pH, temperature, solvent dielectric constant, ionic strength, primary sequence, local polypeptide conformation and tertiary structure. The amino acid residues adjacent to Asn in the peptide chain affect deamidation rates. Gly and Ser following an Asn in protein sequences results in a higher susceptibility to deamidation.

In certain embodiments, the liquid formulation for use in a method of treatment described in the present disclosure may be preserved under conditions of pH and humidity to prevent deamidation of the protein product.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

Intravenous (IV) formulations may be the preferred administration route in particular instances, such as when a patient is in the hospital after transplantation receiving all drugs via the IV route. In certain embodiments, the liquid formulation is diluted with 0.9% Sodium Chloride solution before administration. In certain embodiments, the diluted drug product for injection is isotonic and suitable for administration by intravenous infusion.

In certain embodiments, a salt or buffer component may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

A preservative may be optionally added to the formulations herein to reduce bacterial action. The addition of a preservative may, for example, facilitate the production of a multi-use (multiple-dose) formulation.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

VII. Dosage Regimen

In one aspect, provided herein is sustained-delivery formulation of a peptide comprising a Lung-specific Targeting-Peptide (LTP) (e.g., SEQ ID NO: 1 or SEQ ID NO: 2 (or a cyclized version of the peptide)) linked to a drug or therapeutic agent. In another aspect, provided herein is sustained-delivery formulation of a peptide comprising a cyclic peptide linked to a drug or therapeutic agent. In certain embodiments, the formulation uses a controlled release system. In certain embodiments, the formulation uses a slow release system. In certain embodiments, a sustained-delivery formulation of the present disclosure includes a peptide comprising an LTP comprising the amino acid sequence of SEQ ID NO: 1 linked to a therapeutic agent. In certain embodiments, a sustained-delivery formulation of the present disclosure includes a peptide comprising an LTP comprising the amino acid sequence of SEQ ID NO: 2 linked to a therapeutic agent.

In certain embodiments, the formulation delivers a peptide comprising a Lung-specific Targeting-Peptide (LTP)

(e.g., SEQ ID NO: 1 or SEQ ID NO: 2 (or a cyclized version of the peptide)) of the present disclosure linked to a therapeutic agent over a period of at least 6 hours (e.g., 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours). In certain embodiments, the formulation delivers a peptide comprising an LTP represented by SEQ ID NO: 1 linked to a drug or therapeutic over a period of at least 15 minutes (e.g., 15 minutes, 30 minutes, 45 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours). In certain embodiments, the formulation delivers a peptide comprising an LTP represented by SEQ ID NO: 2 linked to a drug or therapeutic over a period of at least 15 minutes (e.g., 15 minutes, 30 minutes, 45 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours).

In certain embodiments, the formulation delivers a peptide of the present disclosure (e.g., SEQ ID NO: 1 or SEQ ID NO: 2 (or a cyclized version of the peptide)) linked to a therapeutic agent over a period of 15 minutes, 30 minutes, 45 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In certain embodiments, the formulation delivers a peptide comprising an LTP represented by SEQ ID NO: 1 (or a cyclized version of the peptide) linked to a drug or therapeutic over a period of 15 minutes, 30 minutes, 45 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In certain embodiments, the formulation delivers a peptide comprising an LTP represented by SEQ ID NO: 2 (or a cyclized version of the peptide) linked to a drug or therapeutic over a period of 15 minutes, 30 minutes, 45 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours.

In certain embodiments, the formulation delivers a peptide of the present disclosure (e.g., SEQ ID NO: 1 or SEQ ID NO: 2 (or a cyclized version of the peptide)) linked to a therapeutic agent at least once daily (e.g., once a day, twice a day, three times a day). In certain embodiments, the formulation delivers a peptide comprising an LTP represented by SEQ ID NO: 1 (or a cyclized version of the peptide) linked to a drug or therapeutic at least once daily (e.g., once a day, twice a day, three times a day). In certain embodiments, the formulation delivers a peptide comprising an LTP represented by SEQ ID NO: 2 (or a cyclized version of the peptide) linked to a drug or therapeutic at least once daily (e.g., once a day, twice a day, three times a day).

In certain embodiments, the formulation delivering a peptide of the present disclosure (e.g., SEQ ID NO: 1 or SEQ ID NO: 2 (or a cyclized version of the peptide)) linked to a therapeutic agent is administered at least once a week (e.g., once a week, twice a week, 3, 4, 5, 6, 7, or more times a week). In certain embodiments, the formulation delivering a peptide comprising an LTP represented by SEQ ID NO: 1 therapeutic is administered at least once a week (e.g., once a week, twice a week, 3, 4, 5, 6, 7, or more times a week). In certain embodiments, the formulation delivering a peptide comprising an LTP represented by SEQ ID NO: 2 (or a cyclized version of the peptide) linked to a drug or therapeutic is administered at least once a week (e.g., once a week, twice a week, 3, 4, 5, 6, 7, or more times a week).

In some embodiments, the formulation delivering a peptide of the present disclosure (e.g., SEQ ID NO: 1 or SEQ ID NO: 2 (or a cyclized version of the peptide)) linked to a therapeutic agent is a sustained release formulation administered about once per month, about once per every 2 months, about once per every 3 months, about once per every 2 weeks, about once per every 3 weeks, about once per every 4 weeks, about once per every 5 weeks, about once per every 6 weeks, about once per every 7 weeks, about once per every 8 weeks, about once per every 9 weeks, or about once per every 10 weeks. In certain embodiments, the formulation delivering a peptide comprising an LTP represented by SEQ ID NO: 1 (or a cyclized version of the peptide) linked to a drug or therapeutic agent is a sustained release formulation administered about once per month, about once per every 2 months, about once per every 3 months, about once per every 2 weeks, about once per every 3 weeks, about once per every 4 weeks, about once per every 5 weeks, about once per every 6 weeks, about once per every 7 weeks, about once per every 8 weeks, about once per every 9 weeks, or about once per every 10 weeks. In certain embodiments, the formulation delivering a peptide comprising an LTP represented by SEQ ID NO: 2 (or a cyclized version of the peptide) linked to a drug or therapeutic agent is a sustained release formulation administered about once per month, about once per every 2 months, about once per every 3 months, about once per every 2 weeks, about once per every 3 weeks, about once per every 4 weeks, about once per every 5 weeks, about once per every 6 weeks, about once per every 7 weeks, about once per every 8 weeks, about once per every 9 weeks, or about once per every 10 weeks.

In some embodiments, a peptide of the present disclosure (e.g., SEQ ID NO: 1 or SEQ ID NO: 2 (or a cyclized version of the peptide)) linked to a therapeutic agent is administered at a rate of about 100 mg, 200 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg over a period of 24 hours, for example, the first 24 hour period of administration. In some embodiments, a formulation described herein is administered at a rate of between 100 mg and 500 mg, between 100 mg and 1000 mg, between 500 mg and 1000 mg, between 700 mg and 1000 mg, between 700 mg and 1500 mg, between 1200 mg and 1500 mg, between 1000 mg and 1500 mg, between 1000 mg and 2000 mg, between 1500 mg and 2000 mg, between 1700 mg and 2000 mg, between 800 mg and 1200 mg, between 800 and 1000 mg, between 800 mg and 1600 mg, between 600 mg and 800 mg, between 400 mg and 600 mg, or between 900 and 1200 mg over a period of 24 hours, for example, the first 24 hour period of administration. In some embodiments, a peptide of the present disclosure (e.g., SEQ ID NO: 1 or SEQ ID NO: 2 (or a cyclized version of the peptide)) linked to a therapeutic agent is administered in the form of a formulation that is administered orally, intravenously, enterally, parenterally, topically, by inhalation, by injection, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidally, intraspinally, by epidural or infrasternal injection, or by infusion.

In some embodiments, a formulation described herein can be administered by an infusion protocol. For example, in some embodiments, a formulation can be administered, for example, by infusion, for example, in the form of a saline solution, where the solution includes a peptide of the present disclosure (e.g., SEQ ID NO: 1 or SEQ ID NO: 2 (or a cyclized version of the peptide)) linked to a therapeutic agent. In some embodiments the peptide linked to a therapeutic agent is administered to a patient in an amount of about 25 mg, 50 mg, 75 mg, 100 mg, 110 mg, 125 mg, 130 mg, 140 mg, 150 mg, 160 mg, 175 mg, 200 mg, 225 mg, 250 mg, 275 mg, 300 mg, 325 mg, 350 mg, 360 mg, 375 mg, 400 mg, 450 mg, 500 mg, 600 mg, 700 mg, 720 mg, 750 mg, 0 mg to 100 mg, 50 mg to 150 mg, 50 mg, to 100 mg, 100 mg to 200 mg, 200 mg to 300 mg, 200 mg to 400 mg, 200 mg to 500 mg, 100 mg to 150 mg, 100 mg to 500 mg, 150 mg to 300 mg, 100 mg to 360 mg, 100 mg to 400 mg, 300 mg to 500 mg, 300 mg to 600 mg, 300 mg to 600 mg, or 300 mg to 700 mg over a period of about 5 minutes, 10 minutes, 20 minutes, 30 minutes, 40 minutes, 50 minutes, 60 minutes, 90 minutes, 2 hours, 3 hours, 4 hours, 5 hours, 6 hours, 7 hours, 8 hours 9 hours 10 hours, 11 hours, 12 hours, 13 hours, 14 hours 15 hours 16 hours 17 hours, 18 hours, 1 day, 2 days, 3 days 4 days, 5 days, 6 days, or 1 week.

In some embodiments, a formulation described herein can be administered by an infusion protocol. For example, in some embodiments, a formulation can be administered, for example, by infusion, for example, in the form of a saline solution, where the solution includes a peptide of the present disclosure (e.g., SEQ ID NO: 1 or SEQ ID NO: 2 (or a cyclized version of the peptide)) linked to a therapeutic agent. In some embodiments the peptide linked to a therapeutic agent is administered to a patient in an amount of about 25 mg, 50 mg, 75 mg, 100 mg, 110 mg, 125 mg, 130 mg, 140 mg, 150 mg, 160 mg, 175 mg, 200 mg, 225 mg, 250 mg, 275 mg, 300 mg, 350 mg, 400 mg, 450 mg, 500 mg, 0 mg to 100 mg, 50 mg to 150 mg, 50 mg, to 100 mg, 100 mg to 200 mg, 200 mg to 300 mg, 200 mg to 400 mg, 200 mg to 500 mg, 100 mg to 150 mg, 100 mg to 500 mg, or 150 mg to 300 mg over about the first 1 minute, 3 minutes, 5 minutes, 7 minutes, 10 minutes, 12 minutes, 15 minutes, 20 minutes, or 30 minutes of infusion; after which the peptide linked to the therapeutic agent is administered to the patient in an amount of about 25 mg, 50 mg, 75 mg, 100 mg, 110 mg, 125 mg, 130 mg, 140 mg, 150 mg, 160 mg, 175 mg, 200 mg, 225 mg, 250 mg, 275 mg, 300 mg, 325 mg, 350 mg, 360 mg, 375 mg, 400 mg, 450 mg, 500 mg, 600 mg, 700 mg, 720 mg, 750 mg, 0 mg to 100 mg, 50 mg to 150 mg, 50 mg, to 100 mg, 100 mg to 200 mg, 200 mg to 300 mg, 200 mg to 400 mg, 200 mg to 500 mg, 100 mg to 150 mg, 100 mg to 500 mg, 150 mg to 300 mg, 100 mg to 360 mg, 100 mg to 400 mg, 300 mg to 500 mg, 300 mg to 600 mg, 300 mg to 600 mg, or 300 mg to 700 mg over the next 1 hour, 2 hours, 3 hours, 4 hours, 5 hours, 6 hours, 7 hours, 8 hours, 9 hours, 10 hours, 11 hours, 12 hours, 13 hours, 14 hours, or 15 hours of infusion; after which the peptide linked to the therapeutic agent is administered to the patient in an amount of about 25 mg, 50 mg, 75 mg, 100 mg, 110 mg, 125 mg, 130 mg, 140 mg, 150 mg, 160 mg, 175 mg, 200 mg, 225 mg, 250 mg, 275 mg, 300 mg, 325 mg, 350 mg, 360 mg, 375 mg, 400 mg, 450 mg, 475 mg, 500 mg, 510 mg, 520 mg, 530 mg, 540 mg, 550 mg, 560 mg, 570 mg, 580 mg, 590 mg, 600 mg, 700 mg, 720 mg, 750 mg, 800 mg, 900 mg, 950 mg, 1000 mg, 1050 mg, 1080 mg, 0 mg to 100 mg, 50 mg to 150 mg, 50 mg, to 100 mg, 100 mg to 200 mg, 200 mg to 300 mg, 200 mg to 400 mg, 200 mg to 500 mg, 100 mg to 150 mg, 100 mg to 500 mg, 150 mg to 300 mg, 100 mg to 360 mg, 100 mg to 400 mg, 300 mg to 500 mg, 300 mg to 600 mg, 300 mg to 600 mg, or 300 mg to 700 mg, 100 mg to 550 mg, 200 mg to 550 mg, 300 mg to 550 mg, 400 mg to 550 mg, 500 mg to 600 mg, 500 mg to 700 mg, 500 mg to 800 mg, 500 mg to 900 mg, 500 mg to 1000 mg, 500 mg to 1100 mg, or 400 mg to 1100 mg over the next 30 minutes, 1 hour, 2 hours 3 hours, 4 hours, 5 hours, 6 hours, 7 hours, 8 hours, 9 hours, 10 hours, 11 hours, 12 hours, 13 hours, 14 hours, 15 hours, 16 hours, 17 hours 18 hours, 19 hours, 20 hours, 21 hours, 22 hours, 23 hours, 24 hours, 30 hours, or 36 hours of infusion. In a particular embodiment, the peptide linked to the therapeutic agent is administered to the patient in an amount of about 150 mg over the first 10 minutes of infusion, followed by 360 mg over the next 6 hours, and followed by 540 mg over the next 18 hours.

In some embodiments, a formulation described herein is administered, for example, by infusion, where a peptide described herein (e.g., SEQ ID NO: 1 or SEQ ID NO: 2 (or a cyclized version of the peptide)) linked to a therapeutic agent is administered at a specified rate after about the first 24 hours of administration. For example, in some embodiments described herein, after the first 24 hours of administration, the peptide linked to a therapeutic agent is administered to a patient in an amount of about 25 mg, 50 mg, 75 mg, 100 mg, 110 mg, 125 mg, 130 mg, 140 mg, 150 mg, 160 mg, 175 mg, 200 mg, 225 mg, 250 mg, 275 mg, 300 mg, 325 mg, 350 mg, 360 mg, 375 mg, 400 mg, 450 mg, 475 mg, 500 mg, 510 mg, 520 mg, 530 mg, 540 mg, 550 mg, 560 mg, 570 mg, 580 mg, 590 mg, 600 mg, 700 mg, 720 mg, 750 mg, 800 mg, 900 mg, 950 mg, 1000 mg, 1050 mg, 1080 mg, 1100 mg, 1200 mg, 1300 mg, 1400 mg, 1500 mg, 1600 mg, 0 mg to 100 mg, 50 mg to 150 mg, 50 mg, to 100 mg, 100 mg to 200 mg, 200 mg to 300 mg, 200 mg to 400 mg, 200 mg to 500 mg, 100 mg to 150 mg, 100 mg to 500 mg, 100 mg to 600 mg, 150 mg to 300 mg, 100 mg to 360 mg, 100 mg to 400 mg, 300 mg to 500 mg, 300 mg to 600 mg, 300 mg to 600 mg, or 300 mg to 700 mg, 100 mg to 550 mg, 200 mg to 550 mg, 300 mg to 550 mg, 400 mg to 550 mg, 400 mg to 600 mg, 500 mg to 600 mg, 500 mg to 700 mg, 500 mg to 800 mg, 500 mg to 900 mg, 500 mg to 1000 mg, 500 mg to 1100 mg, 600 mg to 800 mg, 600 mg to 1000 mg, 1000 mg to 1500 mg, 1000 mg to 1200 mg, 1000 mg to 1400 mg, 1100 mg to 1500 mg, or 400 mg to 1100 mg over 30 minutes, 1 hour, 2 hours 3 hours, 4 hours, 5 hours, 6 hours, 7 hours, 8 hours, 9 hours, 10 hours, 11 hours, 12 hours, 13 hours, 14 hours, 15 hours, 16 hours, 17 hours 18 hours, 19 hours, 20 hours, 21 hours, 22 hours, 23 hours, 24 hours, 27 hours, 30 hours, or 36 hours following the first 24 hours of administration. in a particular embodiment described herein, after the first 24 hours of administration, the peptide linked to a therapeutic agent is administered to a patient in an amount of about 720 mg over 24 hours following the first 24 hours of administration. In embodiments described herein, the aforementioned administration may be continued for a period of about 1 day, 2 days, 3 days, 4 days, 5 days, 6 days, 1 week, 10 days, 12 days, 2 weeks, 15 days, 18 days, 20 days, 3 weeks, 4 weeks, 5 weeks, 6 weeks, 7 weeks, 8 weeks 9 weeks, 10 weeks, 11 weeks, 12 weeks, or longer.

In some embodiments, a formulation described herein is administered, for example, by infusion or subcutaneously, where a peptide described herein (e.g., SEQ ID NO: 1 or SEQ ID NO: 2 (or a cyclized version of the peptide)) linked to a therapeutic agent is administered to achieve a serum circulating level of the therapeutic of about 10-2500 ng/mL in a patient. For example, in some embodiments described herein, after the first 24 hours of administration, the peptide linked to the therapeutic agent is administered to a patient in an amount to achieve a serum circulating level of about 10 ng/mL, 25 ng/mL, 50 ng/mL, 75 ng/mL, 100 ng/mL, 110 ng/mL, 125 ng/mL, 130 ng/mL, 140 ng/mL, 150 ng/mL, 160 ng/mL, 175 ng/mL, 200 ng/mL, 225 ng/mL, 250 ng/mL, 275 ng/mL, 300 ng/mL, 325 ng/mL, 350 ng/mL, 360 ng/mL, 375 ng/mL, 400 ng/mL, 450 ng/mL, 475 ng/mL, 500 ng/mL, 510 ng/mL, 520 ng/mL, 530 ng/mL, 540 ng/mL, 550 ng/mL, 560 ng/mL, 570 ng/mL, 580 ng/mL, 590 ng/mL, 600 ng/mL, 700 ng/mL, 720 ng/mL, 750 ng/mL, 800 ng/mL, 900 ng/mL, 950 ng/mL, 1000 ng/mL, 1050 ng/mL, 1080 ng/mL, 1100 ng/mL, 1200 ng/mL, 1300 ng/mL, 1400 ng/mL, 1500 ng/mL, 1600 ng/mL, 10 ng/mL to 100 ng/mL, 50 ng/mL to 150 ng/mL, 50 ng/mL to 100 ng/mL, 100 ng/mL to 200 ng/mL, 200 ng/mL to 300 ng/mL, 200 ng/mL to 400 ng/mL, 200 ng/mL to 500 ng/mL, 100 ng/mL to 150 ng/mL, 100 ng/mL to 500 ng/mL, 100 ng/mL to 600 ng/mL, 150 ng/mL to 300 ng/mL, 100 ng/mL to 360 ng/mL, 100 ng/mL to 400 ng/mL, 300 ng/mL to 500 ng/mL, 300 ng/mL to 600 ng/mL, 300 ng/mL to 600 ng/mL, or 300 ng/mL to 700 ng/mL, 100 ng/mL to 550 ng/mL, 200 ng/mL to 550 ng/mL, 300 ng/mL to 550 ng/mL, 400 ng/mL to 550 ng/mL, 400 ng/mL to 600 ng/mL, 500 ng/mL to 600 ng/mL, 500 ng/mL to 700 ng/mL, 500 ng/mL to 800 ng/mL, 500 ng/mL to 900 ng/mL, 500 ng/mL to 1000 ng/mL, 500 ng/mL to 1100 ng/mL, 600 ng/mL to 800 ng/mL, 600 ng/mL to 1000 ng/mL, 1000 ng/mL to 1500 ng/mL, 1000 ng/mL to 1200 ng/mL, 1000 ng/mL to 1400 ng/mL, 1100 ng/mL to 1500 ng/mL, or 400 ng/mL to 1100 ng/mL over 30 minutes, 1 hour, 2 hours 3 hours, 4 hours, 5 hours, 6 hours, 7 hours, 8 hours, 9 hours, 10 hours, 11 hours, 12 hours, 13 hours, 14 hours, 15 hours, 16 hours, 17 hours 18 hours, 19 hours, 20 hours, 21 hours, 22 hours, 23 hours, 24 hours, 27 hours, 30 hours, or 36 hours following the first 24 hours of administration. In a particular embodiment described herein, the peptide of SEQ ID NO: 1 or SEQ ID NO: 2 (or a cyclized version of the peptide) linked to the therapeutic agent is administered to a patient in an amount to achieve a serum circulating level of therapeutic agent of about 10 to 2500 ng/mL for 24 hours to 7 days following the first 24 hours of administration. In embodiments described herein, the aforementioned administration may be continued for a period of about 1 day, 2 days, 3 days, 4 days, 5 days, 6 days, 1 week, 10 days, 12 days, 2 weeks, 15 days, 18 days, 20 days, 3 weeks, 4 weeks, 5 weeks, 6 weeks, 7 weeks, 8 weeks 9 weeks, 10 weeks, 11 weeks, 12 weeks, or longer.

VIII. Definitions

The term "LTP" as used herein refers to a Lung-specific Targeting-Peptide. In certain embodiments, the LTP is comprised of 12-amino acids. In certain embodiments, the LTP comprises the amino acid sequence of SEQ ID NO: 1 (or a cyclized version of the peptide). In certain embodiments, the LTP comprises the amino acid sequence of SEQ ID NO: 2 (or a cyclized version of the peptide).

The term "effective amount" as used herein refers to the amount of an active agent (e.g., an LTP of SEQ ID NO: 1 or SEQ ID NO: 2, or a cyclic peptide of the present disclosure) sufficient to effect beneficial or desired results. An effective amount can be administered in one or more administrations, applications or dosages and is not intended to be limited to a particular formulation or administration route.

As used herein, "treat," "treating," and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

As used herein, the term "lung cancer" includes all types of lung cancers at all stages of progression, including but not limited to bronchogenic carcinoma, small cell lung cancer (SCLC), and non-small cell lung cancer (NSCLC) (e.g., adenocarcinoma, squamous cell carcinoma, large-cell undifferentiated carcinoma, salivary gland-type lung carcinoma, and mesothelioma).

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Throughout the description, where compositions are described as having, including, or comprising specific components, or where processes and methods are described as having, including, or comprising specific steps, it is contemplated that, additionally, there are compositions of the present disclosure that consist essentially of, or consist of, the recited components, and that there are processes and methods according to the present disclosure that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present disclosure, whether explicit or implicit herein. For example, where reference is made to a particular compound, that compound can be used in various embodiments of compositions of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present disclosure also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present disclosure remain operable. Moreover, two or more steps or actions may be conducted simultaneously.

The use of any and all examples, or exemplary language herein, for example, "such as" or "including," is intended merely to illustrate better the present disclosure and does not pose a limitation on the scope of the invention unless claimed. No language in the specification should be construed as indicating any non-claimed element as essential to the practice of the present disclosure.

EXAMPLES

The following examples are merely illustrative and are not intended to limit the scope or content of the invention in any way.

Example 1. Identification and Characterization of Lung-specific Targeting Peptides An alanine scan of the cardiac targeting peptide (CTP, APWHLSSQYSRT, SEQ ID NO: 3) was performed, in which each amino acid was replaced sequentially with alanine, resulting in 11 different "alanine mutant" versions of CTP. Solid phase peptide synthesis of the alanine mutants of CTP fluorescently labeled with Cyanine 5.5 (Cy5.5) was conducted using standard fluorenylmethoxycarbonyl protecting group organic synthesis (FMOC) conditions on a Liberty CEM Microwave Peptide Synthesizer. Cleavage of the fully-protected CTP peptide fragment from the 2-chlorotrityl solid support was accomplished using 1% Trifluoroacetic acid (TFA)/methylene chloride (DCM), followed by elution of the peptide using TFA+scavengers, followed by isolation of the crude product by precipitation in Diethyl Ether (EtO2). Fluorescent dye labelling of the N-terminal amine was performed in solution using Cy5.5-NHS (Lumiprobe, Inc). The resulting crude cyclic CTP-Cy5.5 peptide was purified by preparative C-5 Reversed Phase High Performance Liquid Chromatography (RP-HPLC) on a Waters Delta Prep 4000 chromatography system, using standard Acetonitrile/0.1% TFA gradient conditions. Analytical C-5 RP-HPLC characterization on a Waters Alliance chromatography system followed by Matrix-Assisted Laser Desorption/Ionization Time-Of-Flight Mass Spectrometry (MALDI-TOF-MS) analysis on an Applied Biosystems Voyager workstation was used to confirm the expected mass and purity of the final product. For the purposes of nomenclature, the CTP mutants are identified by the original amino acid followed by its numbered position and A to indicate alanine at the substituted position, e.g., R11A indicates arginine at position 11 of CTP substituted with alanine (APWHLSSQYSAT, SEQ ID NO: 2). CTP was also synthesized as a 6-amino acid N-terminal peptide (CTP-A, APWHLS, SEQ ID NO: 4), and as a 6-amino acid C-terminal peptide (CTP-B, SQYSRT, SEQ ID NO: 5).

For in vitro testing, a rat cardiomyoblast cell line, H9C2 was incubated with each of the alanine-scan peptides, including parental peptide CTP and variants CTP-A and CTP-B; each condition was run in triplicate. For the incubation, peptides were received as lyophilized powders and made into 10 mM stock solutions in DMSO. The stock solution was diluted in culture medium to a final concentration of 10 µM for each peptide, and incubated for 30 minutes at 37° C. with H9C2 cells. Following the incubation period, cells were washed extensively with PBS, trypsinized and fluorescence activated cell sorting (FACS) was performed in biological triplicates. Prior to FACS, cells were also stained with a Live-Dead cell stain, and gating was performed on the live cells. Of all peptides tested, CTP-B (SEQ ID NO: 5), CTP-P2A (AAWHLSSQYSRT, SEQ ID NO: 6), CTP-S7A (SEQ ID NO: 1), and CTP-R11A (SEQ ID NO: 2), displayed statistically significantly higher uptake of the fluorescently labeled peptide into H9C2 cells as compared to full-length, parental CTP (SEQ ID NO: 3), leading to further in vivo testing in mice. There was almost a 3-4 fold increase in median fluorescence intensities compared with CTP for S7A peptide and R11A peptide (FIG. 1).

CTP-B, CTP-P2A, CTP-S7A, CTP-R11A and a random negative control peptide (RAN), were further tested in vivo in mice, in triplicate. Wild-type, 6-week old, male and female CD1 mice were weighed and anesthetized. Mice were injected intravenously with the various peptides, each at a dose of 10 mg/kg. Peptides circulated for 15 minutes, after which mice were euthanized and fixed with 3 ml of 10% formalin injected through the left ventricular apex. Multiple organs (heart, lungs, liver, kidney, spleen, brain, large intestines, small intestines, testes/ovaries, and eyeball) were harvested, placed in a 12-well plate, and immediately imaged using a Perkin-Elmer IVIS imaging system using the relevant excitation-emission laser/detector wavelengths. After the imaging was complete, organs were placed in 10% formalin at room temperature. Following overnight fixation in formalin, organs were transferred to 30% sucrose at 4° C. Following overnight incubation in sucrose, all organs were embedded and frozen in optical cutting medium, 10 µm thick sections were cut, mounted with DAPI, and cover-slipped. Slides were imaged using confocal fluorescent microscopy using the same parameters for imaging between mice, peptides and organs, to allow for comparison and quantification of fluorescence intensities in the relevant regions of interest. CTP-B and CTP-P2A showed results similar to what was predicted from in vitro H9C2 transduction (as shown in FIG. 1); surprisingly, however, S7A peptide and R11A peptide did not show significant cardiac uptake, instead displaying uptakes similar to that seen with random (RAN) peptide.

Figure 2:
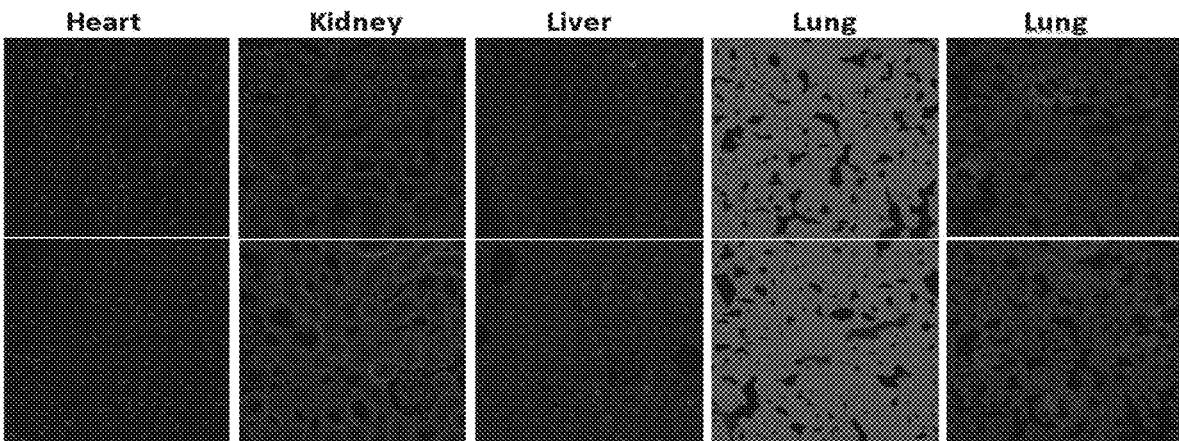
FIG. 2 shows confocal micrographs of heart, kidney, liver and lung tissue from wild-type mice injected with fluorescently-labeled S7A peptide, nuclei stained with DAPI. The first four panels were imaged with the same exposure; the fifth panel shows lung tissue imaged at shorter exposure due to saturation.
Figure 3:
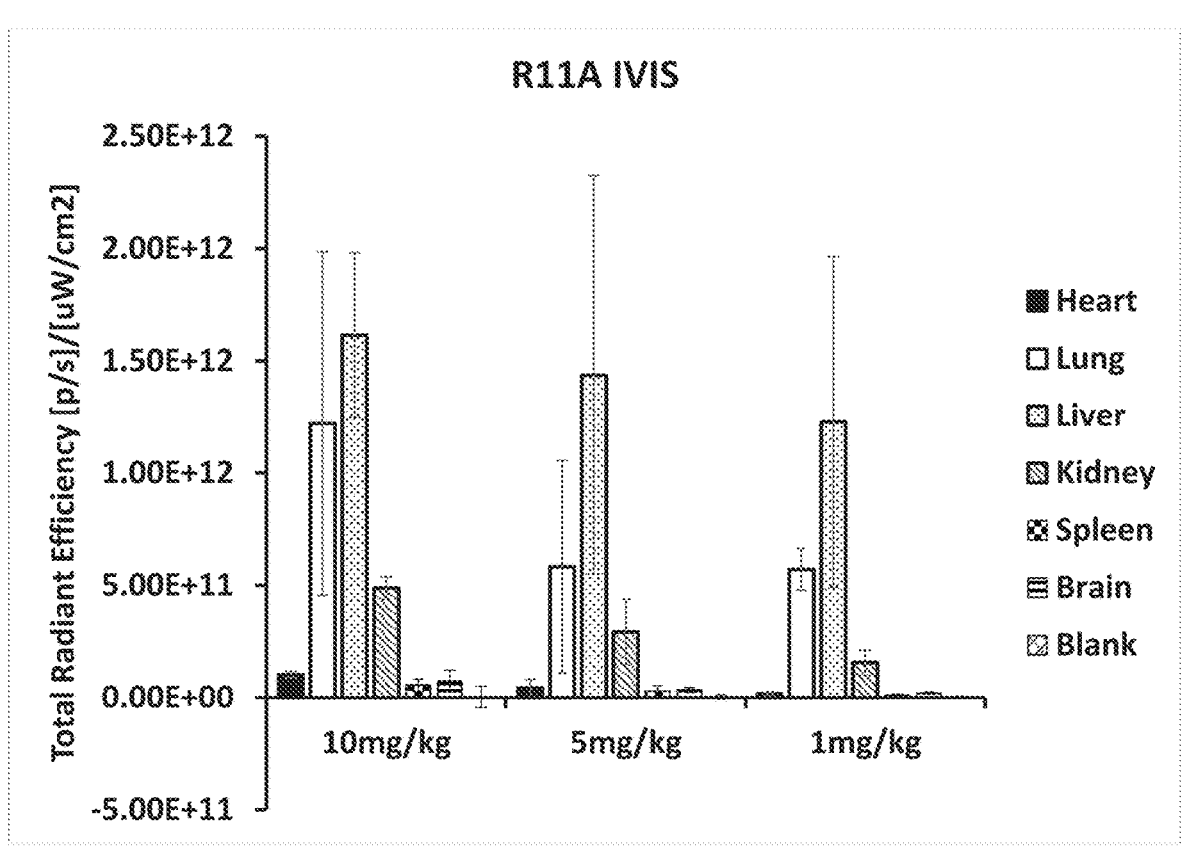
FIG. 3 shows bar graphs depicting quantification of IVIS imaging of ex vivo organs from mice injected with decreasing doses of fluorescently-labeled R11A peptide, 15 minutes post-injection.

Following imaging of the additional organs harvested, S7A peptide and R11A peptide surprisingly displayed robust uptake of both S7A (FIG. 2) and R11A (FIG. 3) in lung epithelial tissue, without significant cardiac uptake (FIG. 3).

Injections were repeated in a total of 9 CD1 mice with identical lung uptake; all images were acquired with the same confocal microscope parameters to allow for cross-animal comparison; however, at the same laser intensity, the lung sample was saturated. Significantly reducing the laser intensities/exposures with higher magnification demonstrated uptake of peptide by lung epithelial tissue (FIG. 2). Wild-type mice were injected with Cy5.5 labeled R11A at a dose of 10 mg/kg, and euthanized mice after 15 minutes; multiple organs were then harvested for imaging. Robust lung uptake of R11A was observed by both confocal microscopy ex vivo imaging of whole organs by IVIS (quantification of IVIS shown in FIG. 3).

Figure 4:
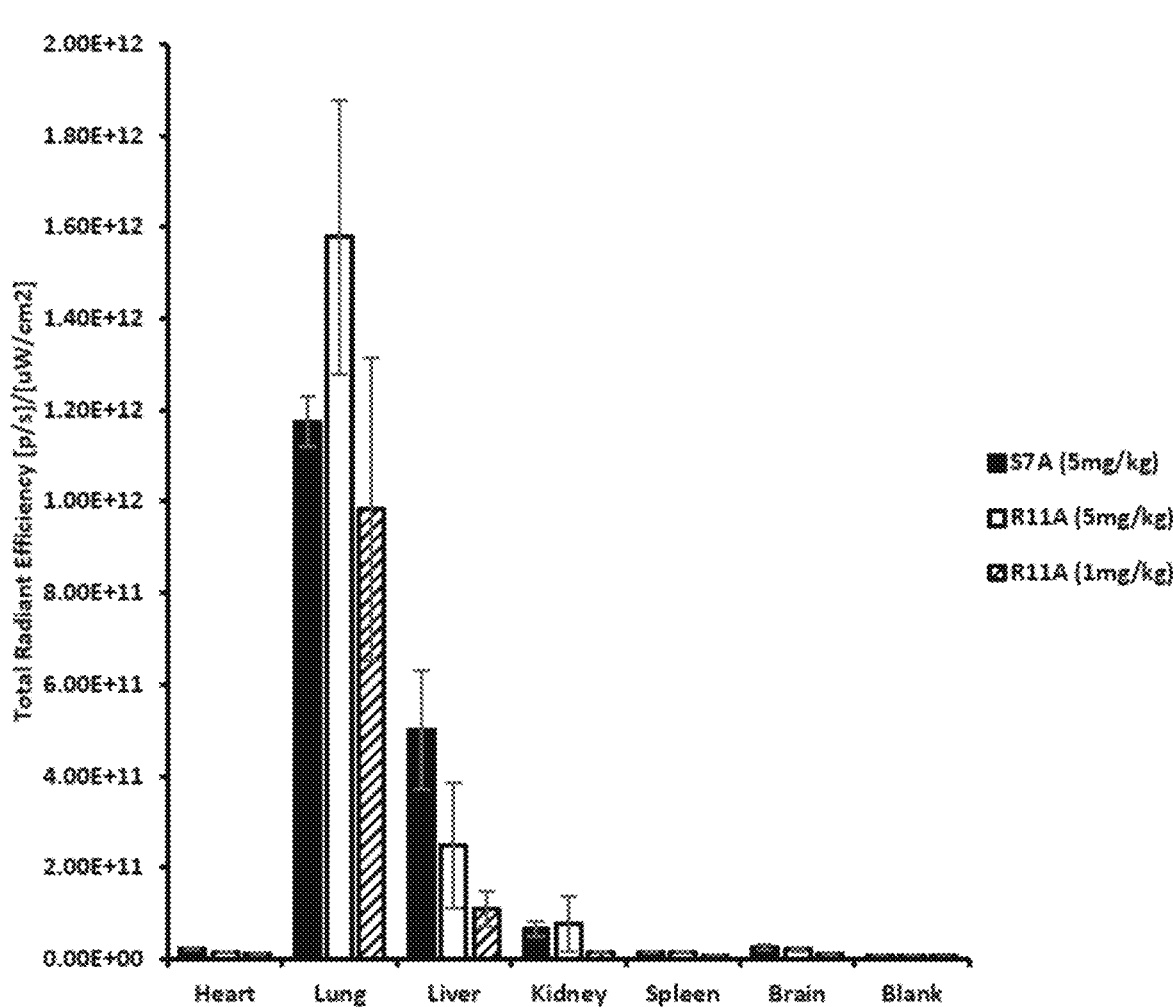
FIG. 4 shows bar graphs depicting quantification of total fluorescence intensity.
Figure 5A:
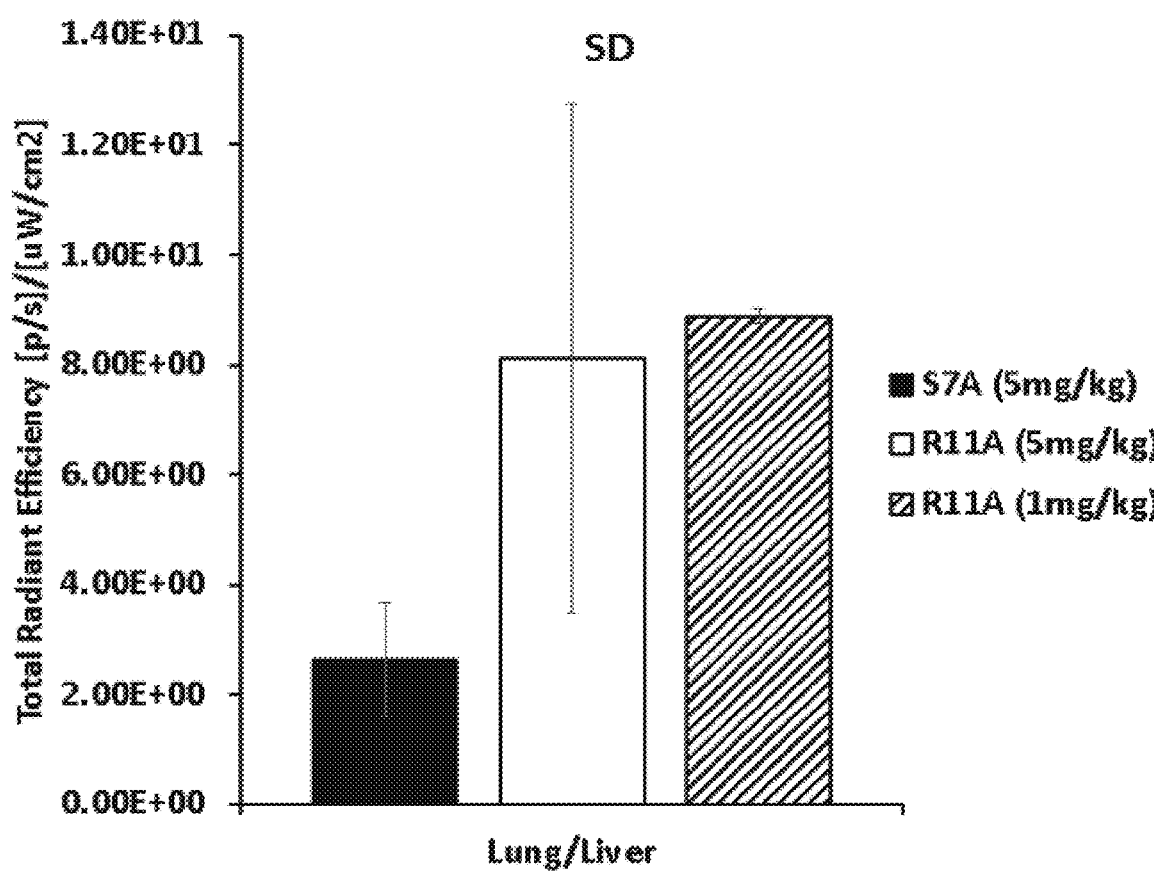
FIGS. 5A-5B show bar graphs depicting the ratio of fluorescence intensities from lung and liver (lung-to-liver ratio) for fluorescently-labeled S7A peptide and R11A peptide at different doses (5 mg/kg or 1 mg/kg).
Figure 5B:
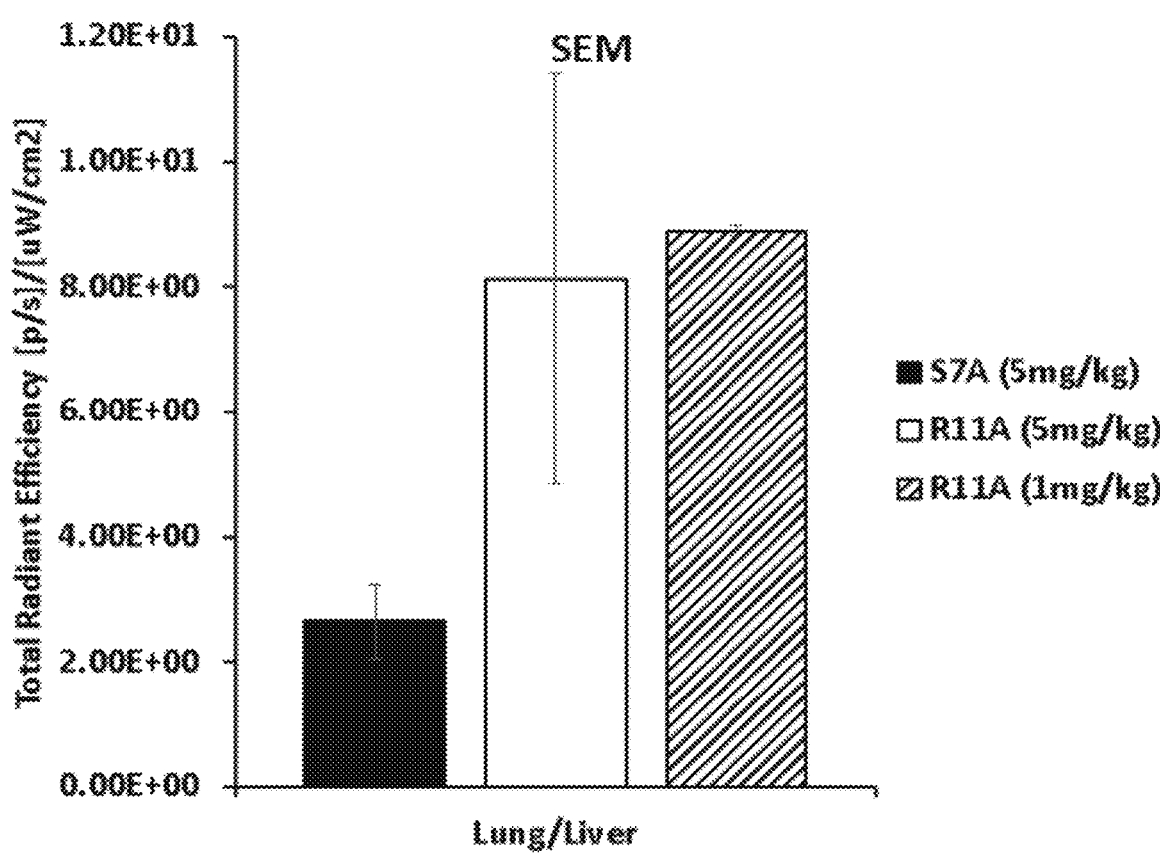

Wild-type CD1 mice were then injected with lower doses of fluorescently labeled S7A peptide (5 mg/kg) or R11A peptide (5 and 1 mg/kg). The peptides were allowed to circulate for 15 minutes, mice were sacrificed, multiple organs were harvested, and ex vivo IVIS imaging was performed. Ex vivo imaging of organs harvested from mice without injected peptides was performed in order to subtract background auto-fluorescent signal from the test organs. IVIS imaging of multiple organs was conducted after administering decreasing doses of peptide from 5 to 1 mg/kg. Robust lung transduction was observed even at the lowest injected dose, with S7A peptide showing approximately 2.5 fold greater lung than liver uptake and with R11A peptide showing 8-9 fold greater lung than liver uptake. Quantification of IVIS imaging for total fluorescent intensity for heart, lung, liver, kidney, spleen, and brain is shown in FIG. 4. Using the fluorescent intensity values, Lung-to-Liver ratios for both peptides were calculated at the tested doses. FIG. 5A displays fluorescent intensity lung-to-liver ratio and standard deviation; FIG. 5B displays fluorescent intensity lung-to-liver ratio and standard error of the mean.

Figure 6A:
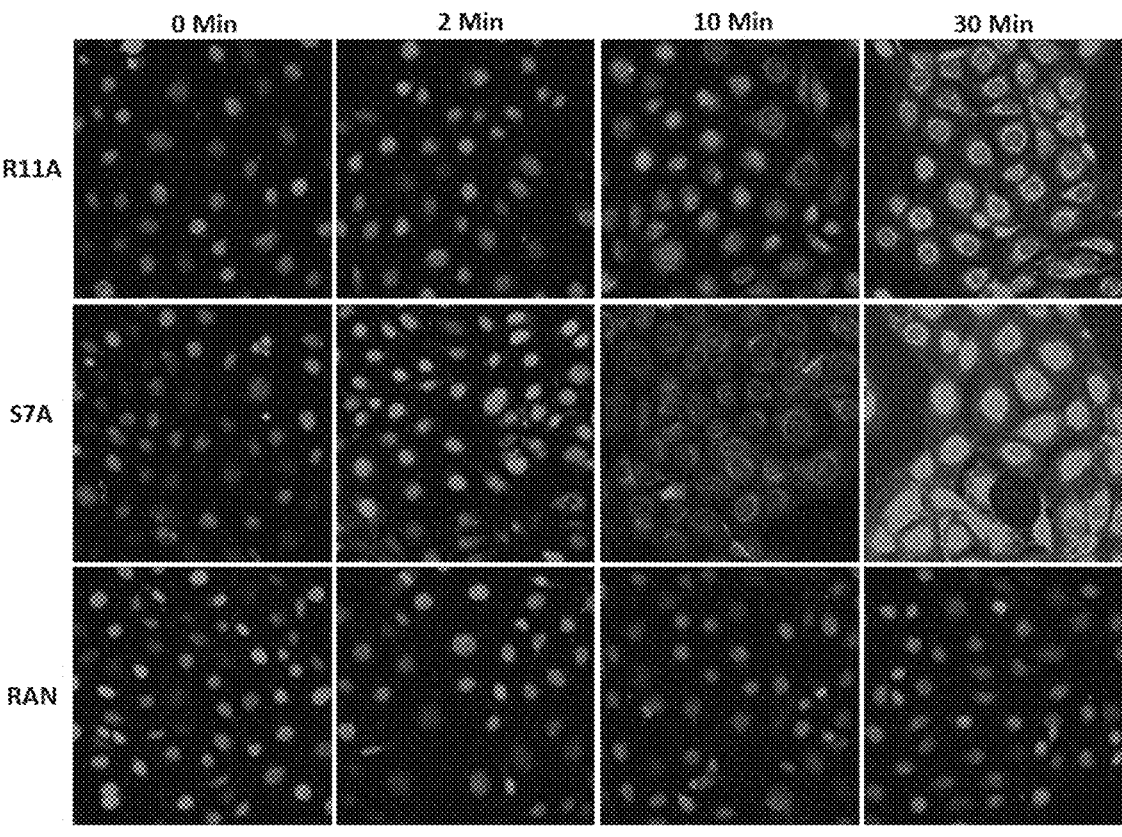
FIG. 6A shows confocal micrographs of human bronchial epithelial cell lines from a cystic fibrosis patient incubated with fluorescently-labeled S7A peptide, R11A peptide, or random ("RAN") peptide for 0 minutes, 2 minutes, 10 minutes, or 30 minutes. DAPI is used as a stain for nuclei.
Figure 6B:
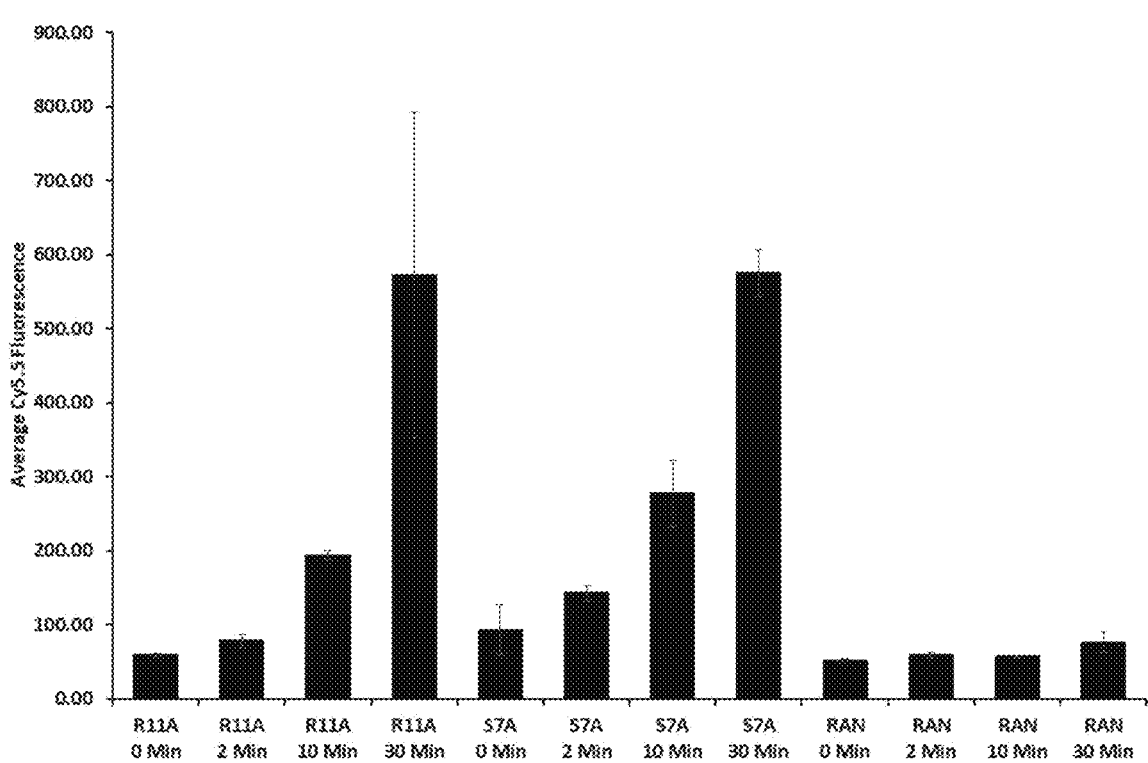
FIG. 6B shows bar graphs depicting average fluorescence intensity.

In order to further confirm that these peptides are readily taken up by lung epithelial cells of relevance, human bronchial epithelial cells from patients with Cystic Fibrosis (CF) were incubated with fluorescently-labeled S7A peptide, R11A peptide, and random peptide ("RAN"). Cells were grown on coverslips, incubated with 10 μM of S7A peptide, R11A peptide, or a random, negative control peptide, for 0, 2, 10, or 30 minutes at 37° C./5% CO2. Following incubation, cells were washed with prewarmed PBS, cross-stained with DAPI, fixed, and mounted on slides for confocal microscopy. Confocal microscopy showed robust uptake of both test peptides, with S7A peptide demonstrating higher uptake and fluorescence intensity even than R11A peptide, and with fluorescence localizing diffusely across the cytoplasm and increasing over time (FIG. 6A). In the time 0 and 2 minute timepoints, only the DAPI nuclear stain is visible, with cytoplasmic staining for the LTPs growing visible at 10 minutes and dominating the field of view at 30 minutes. Quantification of fluorescence intensity further demonstrated significantly high uptake of S7A peptide and R11A peptide (FIG. 6B).

To further characterize uptake of S7A peptide and R11A peptide in cells of interest, human bronchial epithelial cells from patients with CF were grown on cover-slips. Cells were starved at 37° C. for 1 hour in minimal media (MEM media+0.5% Bovine Serum Albumin (BS)+25 mM Hepes buffer at pH 7.4), washed with cold PBS, incubated on ice at 4° C. with fluorescently labeled transferrin (Tf-488) and 10 μM of test peptide (Random, S7A peptide, or R11A peptide) for 1 hour before being shifted to a 37° C. water-bath. Cover-slips were fixed at times 0, 5 and 30 minutes, with random peptide samples fixed only at 0 and 30 minutes. Confocal microscopy imaging revealed robust uptake of S7A peptide and R11A peptide relative to random peptide across all time points collected, showing a very rapid internalization process that was not energy-dependent as it occurred even at 4° C. Furthermore, the peptide did not co-localize with Transferrin, demonstrating that the mechanism of uptake is not through endocytosis.

Example 2. Lung-Specific Targeting Peptides Conjugated to siRNA are Taken up by Human Bronchial Epithelial Cells To further characterize the LTPs as a potential delivery molecule for therapeutic agents, the LTP R11A (SEQ ID NO: 2) and S7A (SEQ ID NO:3) were conjugated by disulfide linker to a number of siRNA molecules, using conjugation techniques known in the art, and tested for uptake by lung epithelial cells. Transformed human bronchial epithelial cells were cultured on glass coverslips as described in Example 2 above. Cells were then cultured with either R11A-siRNA conjugates at a concentration of 5 μM or 10 μM, or S7A-siRNA conjugates at a concentration of 5 μM or 10 μM. Samples were fixed at 0 and 30 minutes for confocal microscopy imaging. As described in Example 1 above, DAPI was used as a stain for nuclei.

Figure 7A:
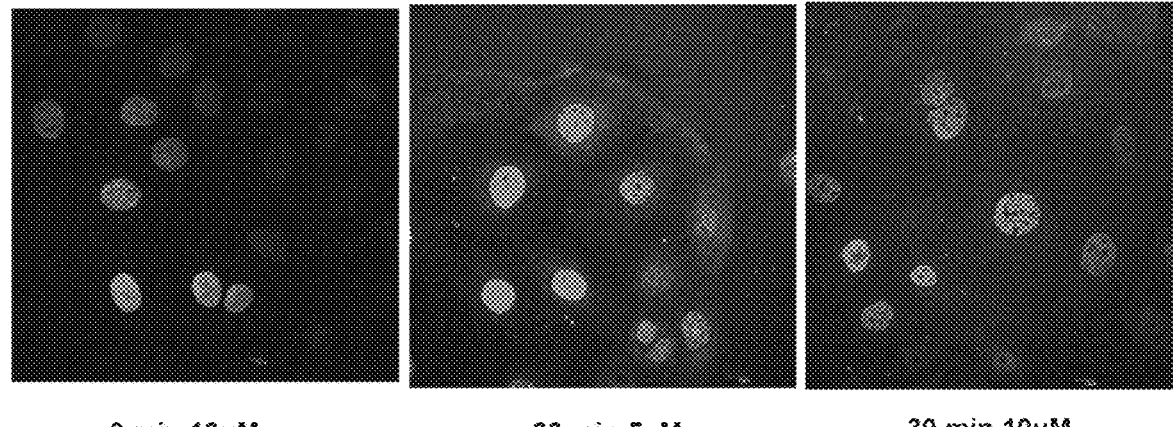
FIGS. 7A-7B show confocal micrographs of human bronchial epithelial cell lines from a cystic fibrosis patient incubated with R11A peptide conjugated to siRNA #1 (FIG. 7A) or siRNA #2 (FIG. 7B).
Figure 7B:
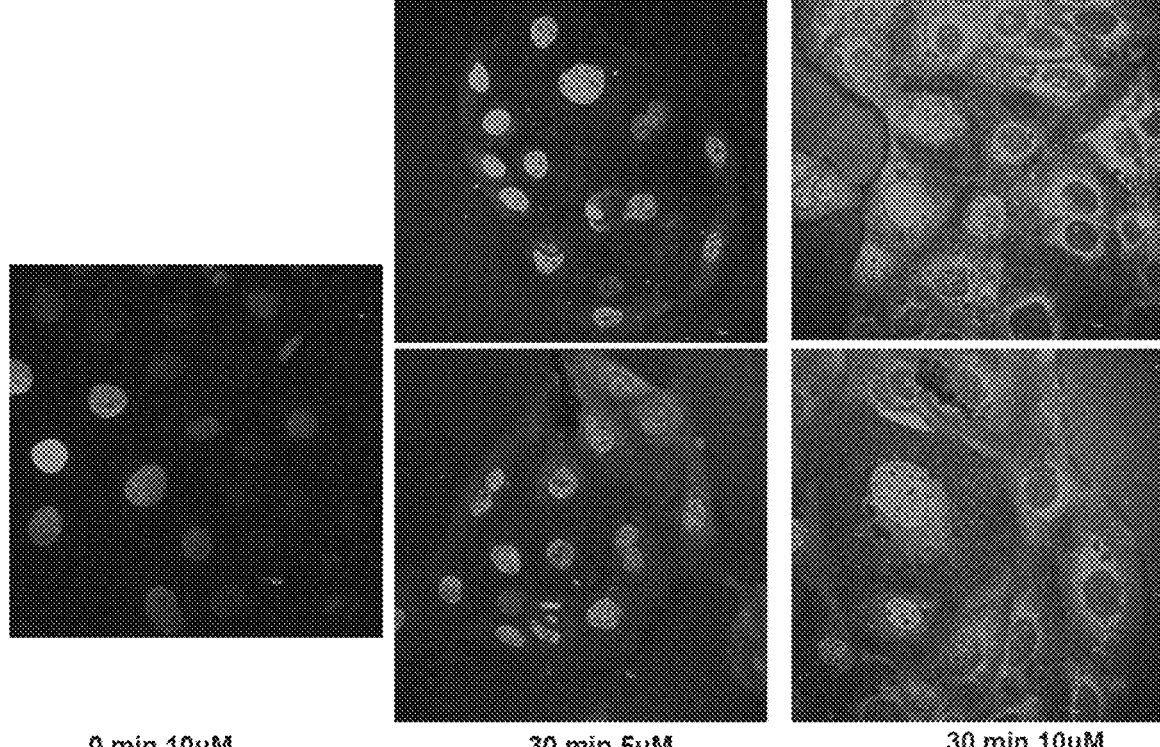
Figure 8A:
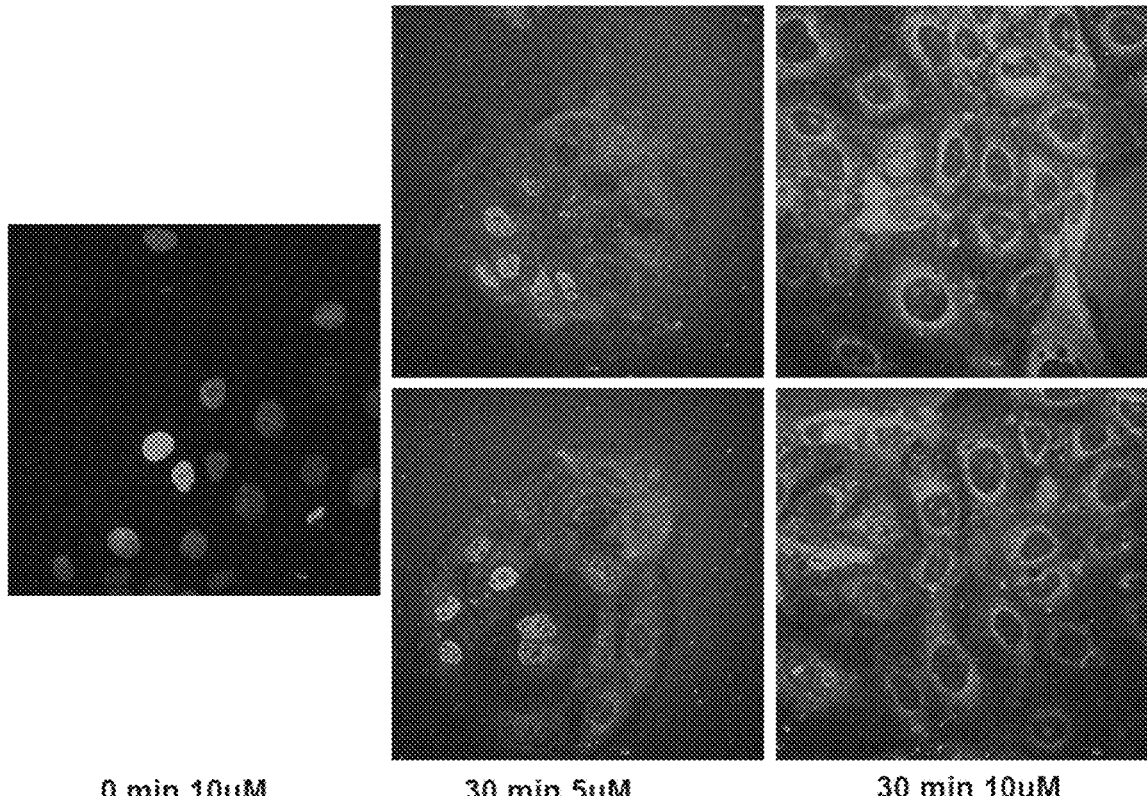
FIGS. 8A-8B show confocal micrographs of human bronchial epithelial cell lines from a cystic fibrosis patient incubated with R11A peptide conjugated to siRNA #1 (FIG. 8A) or siRNA #2 (FIG. 8B). DAPI is used as a stain for nuclei.
Figure 8B:
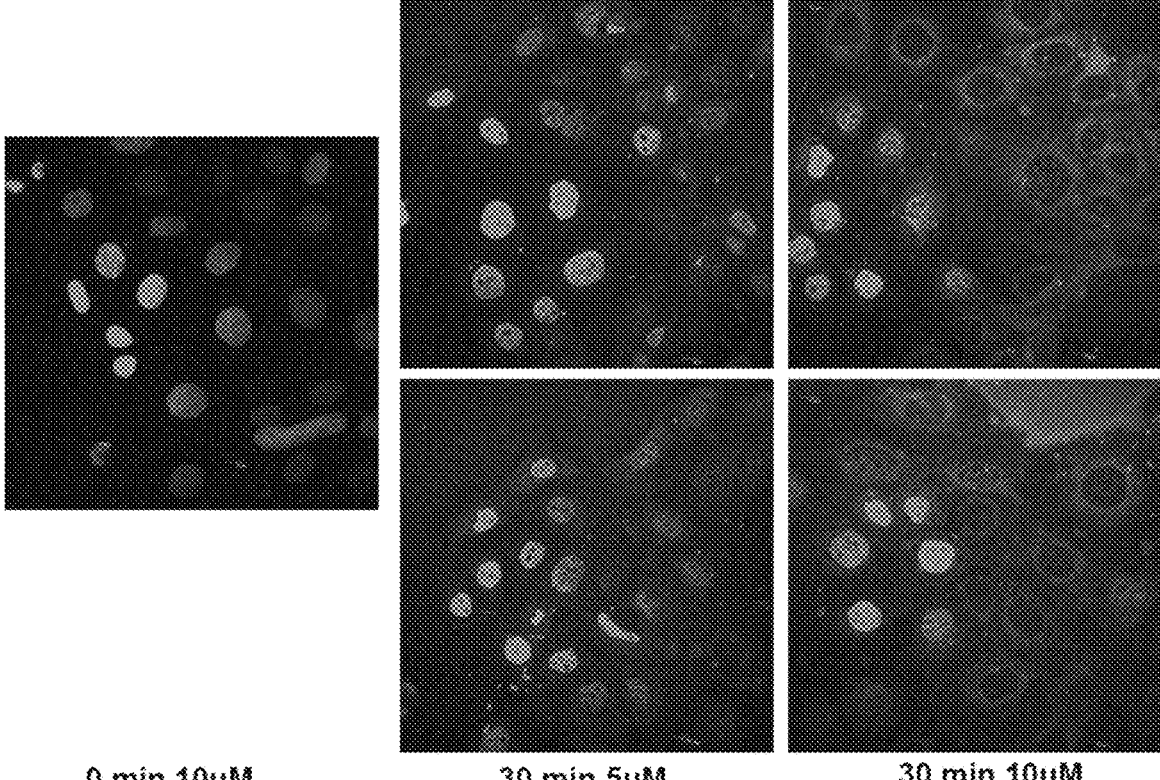

As shown in FIGS. 7A and 7B, at time 0, only the nuclear stain for DAPI was visible, while R11A conjugated to siRNA #1 (FIG. 7A) or #2 (FIG. 7B) was readily taken up by the bronchial cells at 30 minutes post-incubation, evidenced by the cytoplasmic staining. Similarly, S7A conjugated with either siRNA #1 (FIG. 8A) or siRNA #2 (FIG. 8B) showed striking uptake in the bronchial cells, with significant cytoplasmic staining at both tested concentrations. Additional siRNAs were conjugated to either R11A and S7A and tested as above, and each showed uptake by the bronchial cells, to varying degrees, demonstrating that the LTPs connected to moieties such as siRNA are readily taken up by lung epithelial cells.

Figure 9:
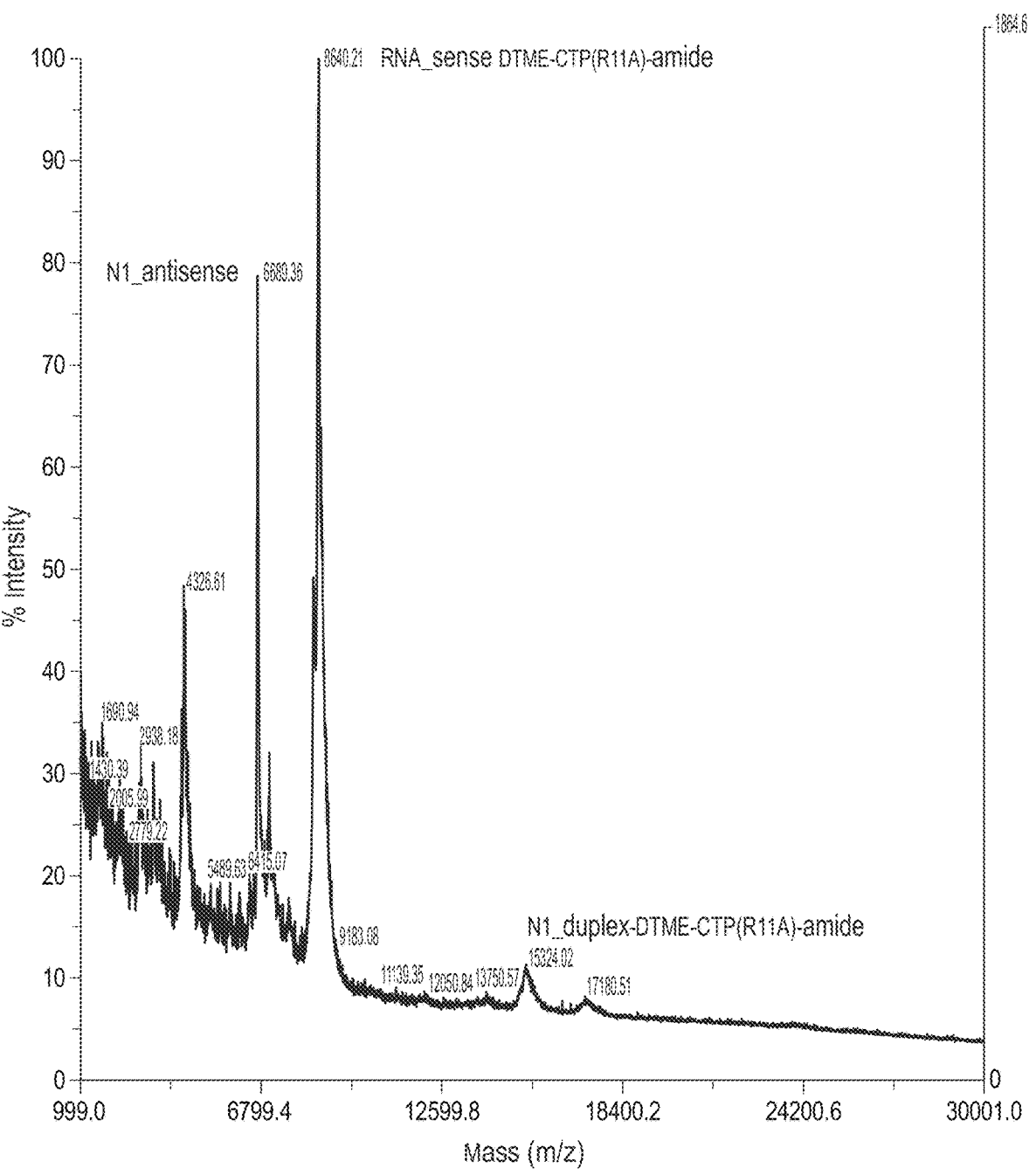
FIG. 9 depicts mass spectrometry analysis of an R11A-siRNA conjugate.

Matrix-assisted laser desorption/ionization time-of-flight mass spectrometry (MALDI-ToF) of an R11A-siRNA conjugate was conducted to confirm the size of LTP-siRNA conjugates was consistent with expected mass and species identity. Lyophilized conjugates were resuspended in nuclease free water prior to analysis of the purified conjugates on an Applied Biosystems Voyager workstation using a 3-hydroxypicolinic acid (3-HPA) matrix in ammonium citrate. As shown in FIG. 9, peaks representing the antisense oligonucleotide, the sense oligonucleotide-LTP peptide, and the oligonucleotide duplex-LTP conjugate were identified, as expected, indicating successful conjugation of the LTP to the siRNA molecule.

Example 3. Analysis of Linear and Cyclic Peptides

The cardiac targeting peptide (CTP, SEQ ID NO: 3) was cyclized by establishing a chemical bond between the amino and carboxyl termini (between the alpha-amino group of N-terminal Lysine and the C-terminus of the peptide sequence), and subsequently labelled with a Cy5.5 fluorescent label at the epsilon amino group of the N-terminal lysine.

31

Figure 10A:
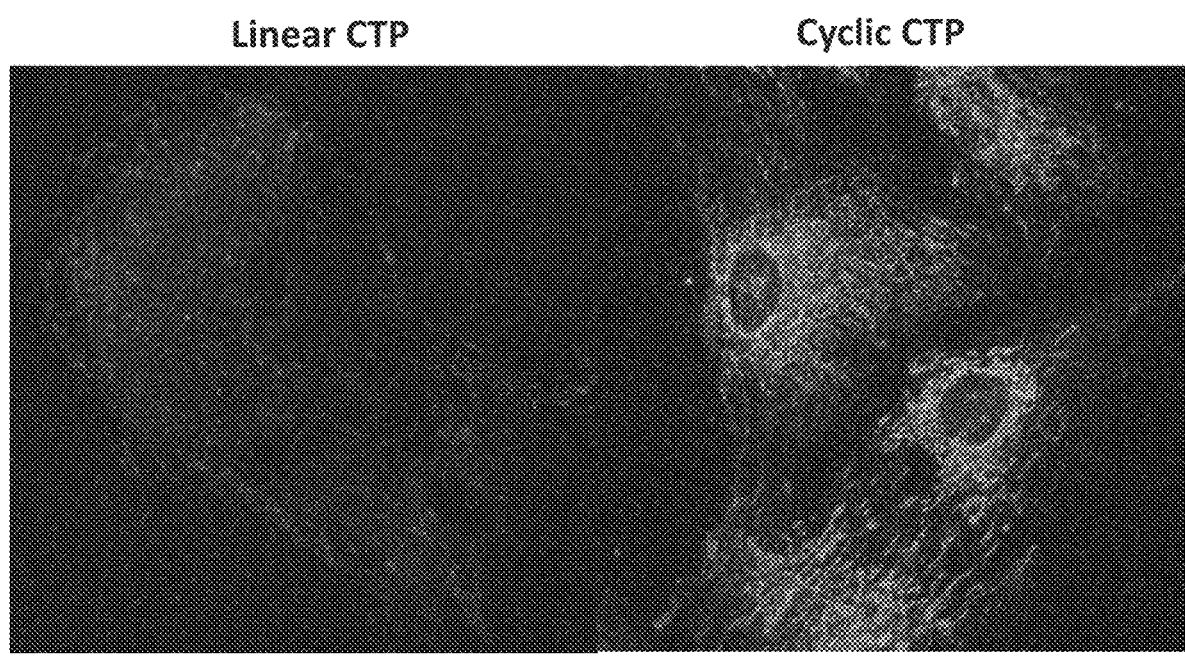
FIG. 10A shows confocal micrographs of rat cardiomyoblast incubated with fluorescently labelled CTP peptide in both linear form (left panel) and cyclic form (right panel).
Figure 10B:
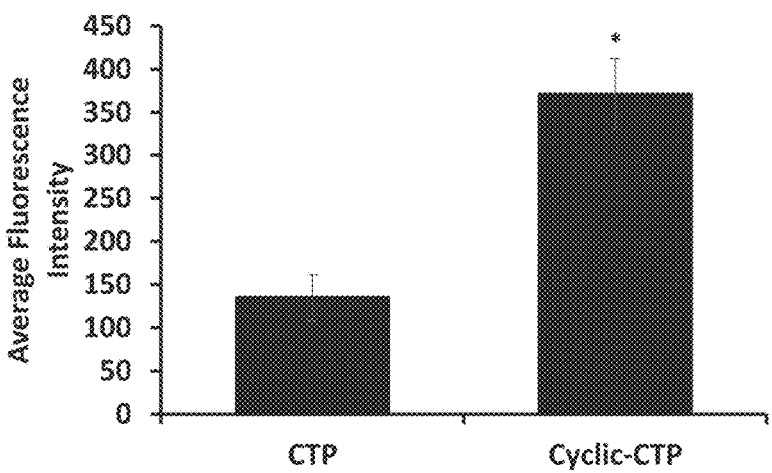
FIG. 10B shows bar graphs depicting average fluorescence intensity of linear and cyclic CTP.

The cyclic form of CTP was then compared to the linear form of CTP using confocal microscopy of transduced H9C2 cells, using the protocol as described in Example 1 above. As shown in FIG. 10A, the cyclic format of the CTP peptide enhanced uptake relative to the linear format of the CTP peptide, as evidenced by the increased fluorescence and more concentrated, punctate staining observed by the confocal imaging. Quantification of the fluorescence intensity, as shown in FIG. 10B and Table 2, confirmed the enhanced fluorescent activity.

TABLE 2

| Quantification of fluorescence from linear or cyclic CTP in transduced H9C2 cells | | | | |
|---|---|---|---|---|
| Sample | Mean | Background | Subtraction | Standard Deviation |
| Linear CTP | 362.478 | 227.701 | 134.777 | 26.590 |
| Cyclic CTP | 521.590 | 150.467 | 371.123 | 40.946 |

Figure 11:
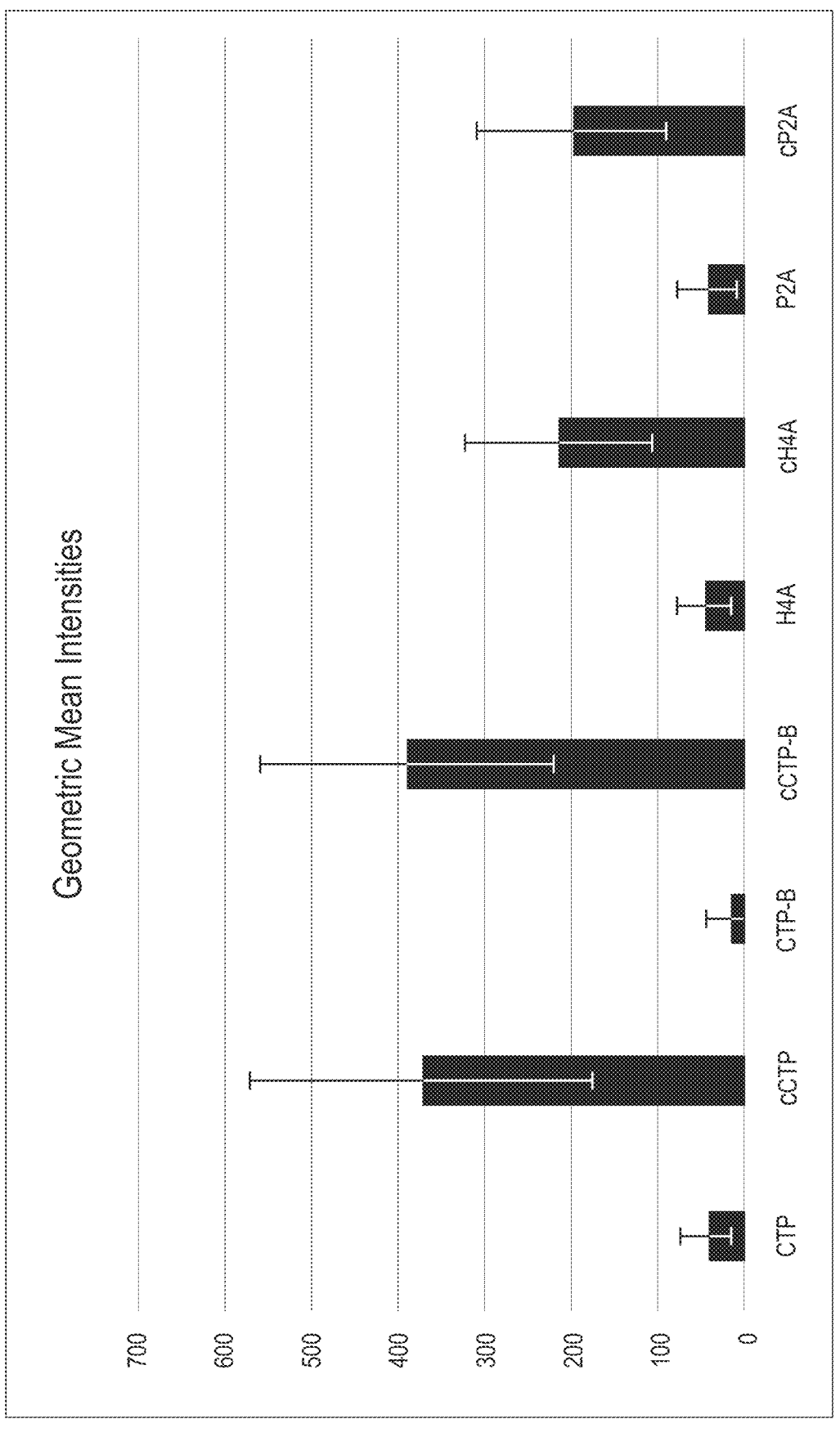
FIG. 11 depicts bar graphs of mean fluorescent intensities of CTP and variants CTP-B, CTP-H4A, and CTP-P2A, in both linear and cyclic forms, as determined by fluorescent activated cell sorting (FACS) analysis.

The variants of CTP generated by the alanine scan (as described in Example 1 above) were then cyclicized, using the methodology described above for the cyclization of CTP, and assessed for transduction efficiency. Fluorescence activated cell sorting (FACS) of CTP and variants CTP-B (SEQ ID NO:5), CTP-H4A (SEQ ID NO:7), and CTP-P2A (SEQ ID NO:6), was conducted for both linear and cyclic formats of the peptides. Bar graphs depicting the mean intensity fluorescence observed by FACS for each tested peptide are depicted in FIG. 11. As shown, each cyclic peptide (referred to in FIG. 11, for example, as "cCTP," for "cyclic CTP") showed significantly higher mean fluorescence intensity as compared to its linear counterpart. These data suggest that cyclization of CTP and its variants, including the LTP peptides S7A and R11A, results in increased transduction efficiency relative to the linear forms of the peptides.

Numbered Embodiments

Embodiments disclosed herein include embodiments 1 to 24, as provided in the numbered embodiments of the disclosure.

Embodiment 1: A compound comprising a recombinant and isolated Lung-specific Targeting-Peptide (LTP) of the sequence of SEQ ID NO: 1 or 2.

Embodiment 2: The compound of embodiment 1, wherein the LTP is optionally further connected to a label at the N- and/or the C-termini.

Embodiment 3: The compound of embodiment 1 or 2, wherein the LTP is optionally further connected to a label at the C-terminus.

Embodiment 4: The compound of any one of embodiments 1 to 3 formulated as a delivery vehicle/agent.

Embodiment 5: The compound of embodiment 4, wherein the LTP is conjugated to a drug or therapeutic, a nanoparticle, a peptide, a protein, a nucleic acid, or a detectable agent.

Embodiment 6: The compound of embodiment 5, wherein the LTP is conjugated to the drug or therapeutic, the nanoparticle, the peptide, the protein, the nucleic acid, or the detectable agent via an ester linkage, disulfide or protease sensitive linkers.

Embodiment 7: The compound of embodiment 5 or 6, wherein the nanoparticle comprises a drug or therapeutic.

Embodiment 8: The compound of any one of embodiments 1 to 7, wherein the LTP is linked to a nucleic acid for gene therapy, a small interfering RNA (siRNA), a small nuclear RNA (snRNA), a non-coding RNA, a microRNA (miRNA), a messenger RNA (mRNA), a catalytic RNA, a catalytic DNA, a DNA origami, an antisense oligonucleotide, a nucleoside analogs, a polynucleic acid decoy, an aptamer, a plasmid, or a nucleic acid vector.

Embodiment 9: The compound of any one of embodiments 1 to 7, wherein the LTP is linked to an ROS scavenger molecule or a γ-secretase inhibitor or a Notch inhibitor.

Embodiment 10: The compound of embodiment 9, wherein the ROS scavenger molecule is selected from the group consisting of glutathione (GSH), Szeto-Schiller peptide (SS-31), Mitotempo, catalase and superoxide dismutase; and wherein the γ-secretase inhibitor or the Notch inhibitor is N—[N-(3,5-difluorophenacetyl-L-alanyl)]-S-phenylglycine t-butyl ester (DAPT).

Embodiment 11: The compound according to embodiment 9 or 10, wherein the ROS scavenger, or the γ-secretase inhibitor or the Notch inhibitor is linked upstream of the N-terminus of the LTP peptide.

Embodiment 12: The compound according to embodiment 11, comprising an ester linkage between the LTP and the ROS scavenger, or the γ-secretase inhibitor or the Notch inhibitor.

Embodiment 13: The compound according to embodiment 12, wherein the ester linkage is an ester linkage cleavable by an intracellular esterase.

Embodiment 14: A formulation comprising a lung-penetrating peptide (LTP) according to any one of embodiments 8 to 13 and a pharmaceutically acceptable carrier.

Embodiment 15: The formulation of embodiment 14 is a sustained-delivery formulation.

Embodiment 16: The formulation of embodiment 13 or 15, wherein the formulation uses a controlled release system.

Embodiment 17: The formulation of embodiment 14 or 15, wherein the formulation uses a slow release system.

Embodiment 18: A method of treating a human subject suffering from lung disease or disorder, the method comprising introducing into the lung tissue of the human subject the compound of any one of embodiments 8 to 13, or a formulation of any one of embodiments 14 to 17.

Embodiment 19: The method of embodiment 18, wherein the subject suffers from a lung disease or disorder selected from the group consisting of chronic obstructive pulmonary disease (COPD), emphysema, chronic bronchitis, asthma, primary ciliary dyskinesia (PCD), cystic fibrosis (CF), and lung cancer.

Embodiment 20: The method of embodiment 19, wherein the lung disease or disorder is chronic obstructive pulmonary disease (COPD).

Embodiment 21: The method of embodiment 19, wherein the lung disease or disorder is asthma.

Embodiment 22: The method of embodiment 19, wherein the lung disease or disorder is cystic fibrosis (CF).

Embodiment 23: The method of embodiment 19, wherein the lung disease or disorder is lung cancer.

Embodiment 24: A method of growing and/or re-cilliating tracheal epithelial cells (MTCs) and/or nasal epithelial cells of a mammal, the method comprising introducing into the lung tissue of the human subject the compound of any one of embodiments 8 to 13, or a formulation of any one of embodiments 14 to 17.

INCORPORATION BY REFERENCE

Unless stated to the contrary, the entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of introducing a cargo into a lung epithelial cell, comprising administering to the lung epithelial cell a formulation comprising an effective amount of a Lung-specific Targeting-Peptide (LTP) connected to the cargo, wherein the LTP comprises the amino acid sequence of SEQ ID NO: 1 or 2, the formulation is effective to introduce the cargo to the lung epithelial cell, and the cargo is a drug or therapeutic, nanoparticle, peptide, protein, nucleic acid, or detectable agent.

2. A formulation comprising a Lung-specific Targeting-Peptide (LTP) connected to a drug or therapeutic, nanoparticle, peptide, protein, nucleic acid, or detectable agent, and a pharmaceutically acceptable carrier, wherein the LTP comprises the amino acid sequence of SEQ ID NO: 1 or 2.

3. The formulation of claim 2, wherein the LTP is further connected to a label at the N- and/or the C-termini.

4. The formulation of claim 2, wherein the LTP is further connected to a label at the C-terminus.

5. The formulation of claim 2, wherein the LTP is conjugated to the drug or therapeutic, the nanoparticle, the peptide, the protein, the nucleic acid, or the detectable agent via an ester linkage, disulfide or protease sensitive linkers.

6. The formulation of claim 2, wherein the LTP is connected to a nucleic acid for gene therapy, a small interfering RNA (siRNA), a small nuclear RNA (snRNA), a non-coding RNA, a microRNA (miRNA), a messenger RNA (mRNA), a catalytic RNA, a catalytic DNA, an antisense RNAo, a nucleoside analog, a polynucleic acid decoy, an aptamer, a plasmid, or a nucleic acid vector.

7. The formulation of claim 2, wherein the LTP is a linear peptide.

8. The formulation of claim 2, formulated as a sustained-delivery formulation.

9. The formulation of claim 2, wherein the formulation uses a controlled release system.

10. The formulation of claim 2, wherein the formulation uses a slow release system.

11. A method of treating a human subject suffering from a lung disease or disorder, the method comprising administering the formulation of claim 2 to the human subject, wherein the formulation is administered in an amount effective to treat the lung disease or disorder.

12. A method of growing and/or re-cilliating tracheal epithelial cells (MTCs) and/or nasal epithelial cells of a mammal, the method comprising administering an effective amount of the formulation of claim 2 to the mammal, wherein the formulation is effective to grow and/or re-cilliate MTCs and/or nasal epithelial cells of a mammal.

13. A cyclic peptide comprising the amino acid sequence of SEQ ID NOs: 1 or 2, wherein an N-terminal lysine is added to the amino acid sequence, wherein the N-terminal lysine connects to the C-terminus of the amino acid sequence, and wherein the cyclic peptide is connected to a nucleic acid.

14. A formulation comprising a Lung-specific Targeting-Peptide (LTP) connected to a nucleic acid and a pharmaceutically acceptable carrier, wherein the LTP is cyclic and comprises the amino acid sequence of SEQ ID NO: 1 or 2.

* * * * *

```
                        SEQUENCE LISTING

<160> NUMBER OF SEQ ID NOS: 28

<210> SEQ ID NO 1
<211> LENGTH: 12
<212> TYPE: PRT
<213> ORGANISM: Artificial Sequence
<220> FEATURE:
<223> OTHER INFORMATION: artificial peptide

<400> SEQUENCE: 1

Ala Pro Trp His Leu Ser Ala Gln Tyr Ser Arg Thr
1               5                   10

<210> SEQ ID NO 2
<211> LENGTH: 12
<212> TYPE: PRT
<213> ORGANISM: Artificial Sequence
<220> FEATURE:
<223> OTHER INFORMATION: artificial peptide

<400> SEQUENCE: 2

Ala Pro Trp His Leu Ser Ser Gln Tyr Ser Ala Thr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: artificial peptide

<400> SEQUENCE: 3

Ala Pro Trp His Leu Ser Ser Gln Tyr Ser Arg Thr
1               5                   10

<210> SEQ ID NO 4
<211> LENGTH: 6
<212> TYPE: PRT
<213> ORGANISM: Artificial Sequence
<220> FEATURE:
<223> OTHER INFORMATION: artificial peptide

<400> SEQUENCE: 4

Ala Pro Trp His Leu Ser
1               5

<210> SEQ ID NO 5
<211> LENGTH: 6
<212> TYPE: PRT
<213> ORGANISM: Artificial Sequence
<220> FEATURE:
<223> OTHER INFORMATION: artificial peptide

<400> SEQUENCE: 5
```

```
Ser Gln Tyr Ser Arg Thr
1               5

<210> SEQ ID NO 6
<211> LENGTH: 12
<212> TYPE: PRT
<213> ORGANISM: Artificial Sequence
<220> FEATURE:
<223> OTHER INFORMATION: artificial peptide

<400> SEQUENCE: 6

Ala Ala Trp His Leu Ser Ser Gln Tyr Ser Arg Thr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: artificial peptide

<400> SEQUENCE: 7

Ala Pro Trp Ala Leu Ser Ser Gln Tyr Ser Arg Thr
1               5                   10

<210> SEQ ID NO 8
<211> LENGTH: 12
<212> TYPE: PRT
<213> ORGANISM: Artificial Sequence
<220> FEATURE:
<223> OTHER INFORMATION: artificial peptide

<400> SEQUENCE: 8

Ala Pro Trp His Ala Ser Ser Gln Tyr Ser Arg Thr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: artificial peptide

<400> SEQUENCE: 9

Ala Pro Trp His Leu Ala Ser Gln Tyr Ser Arg Thr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: artificial peptide

<400> SEQUENCE: 10

Ala Pro Trp His Leu Ser Ser Ala Tyr Ser Arg Thr
1               5                   10

<210> SEQ ID NO 11
<211> LENGTH: 12
<212> TYPE: PRT
<213> ORGANISM: Artificial Sequence
<220> FEATURE:
<223> OTHER INFORMATION: artificial peptide

<400> SEQUENCE: 11
```

-continued

```
Ala Pro Trp His Leu Ser Ser Gln Ala Ser Arg Thr
1               5                   10

<210> SEQ ID NO 12
<211> LENGTH: 12
<212> TYPE: PRT
<213> ORGANISM: Artificial Sequence
<220> FEATURE:
<223> OTHER INFORMATION: artificial peptide

<400> SEQUENCE: 12

Ala Pro Trp His Leu Ser Ser Gln Tyr Ala Arg Thr
1               5                   10

<210> SEQ ID NO 13
<211> LENGTH: 12
<212> TYPE: PRT
<213> ORGANISM: Artificial Sequence
<220> FEATURE:
<223> OTHER INFORMATION: artificial peptide

<400> SEQUENCE: 13

Ala Pro Trp His Leu Ser Ser Gln Tyr Ser Arg Ala
1               5                   10

<210> SEQ ID NO 14
<211> LENGTH: 12
<212> TYPE: PRT
<213> ORGANISM: Artificial Sequence
<220> FEATURE:
<223> OTHER INFORMATION: artificial peptide

<400> SEQUENCE: 14

Ala Pro Ala His Leu Ser Ser Gln Tyr Ser Arg Thr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: artificial peptide

<400> SEQUENCE: 15

Lys Ala Pro Trp His Leu Ser Ala Gln Tyr Ser Arg Thr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: artificial peptide

<400> SEQUENCE: 16

Lys Ala Pro Trp His Leu Ser Ser Gln Tyr Ser Ala Thr
1               5                   10

<210> SEQ ID NO 17
<211> LENGTH: 13
<212> TYPE: PRT
<213> ORGANISM: Artificial Sequence
<220> FEATURE:
<223> OTHER INFORMATION: artificial peptide

<400> SEQUENCE: 17

Lys Ala Pro Trp His Leu Ser Ser Gln Tyr Ser Arg Thr
```

-continued

```
1               5                    10
```

<210> SEQ ID NO 18
<211> LENGTH: 7
<212> TYPE: PRT
<213> ORGANISM: Artificial Sequence
<220> FEATURE:
<223> OTHER INFORMATION: artificial peptide

<400> SEQUENCE: 18

Lys Ala Pro Trp His Leu Ser
1               5

<210> SEQ ID NO 19
<211> LENGTH: 7
<212> TYPE: PRT
<213> ORGANISM: Artificial Sequence
<220> FEATURE:
<223> OTHER INFORMATION: artificial peptide

<400> SEQUENCE: 19

Lys Ser Gln Tyr Ser Arg Thr
1               5

<210> SEQ ID NO 20
<211> LENGTH: 13
<212> TYPE: PRT
<213> ORGANISM: Artificial Sequence
<220> FEATURE:
<223> OTHER INFORMATION: artificial peptide

<400> SEQUENCE: 20

Lys Ala Ala Trp His Leu Ser Ser Gln Tyr Ser Arg Thr
1               5                    10

<210> SEQ ID NO 21
<211> LENGTH: 13
<212> TYPE: PRT
<213> ORGANISM: Artificial Sequence
<220> FEATURE:
<223> OTHER INFORMATION: artificial peptide

<400> SEQUENCE: 21

Lys Ala Pro Trp Ala Leu Ser Ser Gln Tyr Ser Arg Thr
1               5                    10

<210> SEQ ID NO 22
<211> LENGTH: 13
<212> TYPE: PRT
<213> ORGANISM: Artificial Sequence
<220> FEATURE:
<223> OTHER INFORMATION: artificial peptide

<400> SEQUENCE: 22

Lys Ala Pro Trp His Ala Ser Ser Gln Tyr Ser Arg Thr
1               5                    10

<210> SEQ ID NO 23
<211> LENGTH: 13
<212> TYPE: PRT
<213> ORGANISM: Artificial Sequence
<220> FEATURE:
<223> OTHER INFORMATION: artificial peptide

<400> SEQUENCE: 23

Lys Ala Pro Trp His Leu Ala Ser Gln Tyr Ser Arg Thr
1               5                    10

-continued

```
<210> SEQ ID NO 24
<211> LENGTH: 13
<212> TYPE: PRT
<213> ORGANISM: Artificial Sequence
<220> FEATURE:
<223> OTHER INFORMATION: artificial peptide

<400> SEQUENCE: 24

Lys Ala Pro Trp His Leu Ser Ser Ala Tyr Ser Arg Thr
1               5                   10

<210> SEQ ID NO 25
<211> LENGTH: 13
<212> TYPE: PRT
<213> ORGANISM: Artificial Sequence
<220> FEATURE:
<223> OTHER INFORMATION: artificial peptide

<400> SEQUENCE: 25

Lys Ala Pro Trp His Leu Ser Ser Gln Ala Ser Arg Thr
1               5                   10

<210> SEQ ID NO 26
<211> LENGTH: 13
<212> TYPE: PRT
<213> ORGANISM: Artificial Sequence
<220> FEATURE:
<223> OTHER INFORMATION: artificial peptide

<400> SEQUENCE: 26

Lys Ala Pro Trp His Leu Ser Ser Gln Tyr Ala Arg Thr
1               5                   10

<210> SEQ ID NO 27
<211> LENGTH: 13
<212> TYPE: PRT
<213> ORGANISM: Artificial Sequence
<220> FEATURE:
<223> OTHER INFORMATION: artificial peptide

<400> SEQUENCE: 27

Lys Ala Pro Trp His Leu Ser Ser Gln Tyr Ser Arg Ala
1               5                   10

<210> SEQ ID NO 28
<211> LENGTH: 13
<212> TYPE: PRT
<213> ORGANISM: Artificial Sequence
<220> FEATURE:
<223> OTHER INFORMATION: artificial peptide

<400> SEQUENCE: 28

Lys Ala Pro Ala His Leu Ser Ser Gln Tyr Ser Arg Thr
1               5                   10
```